United States Patent
Meadows

(10) Patent No.: US 9,670,518 B2
(45) Date of Patent: Jun. 6, 2017

(54) PRODUCTION OF ACETYL-COENZYME A DERIVED COMPOUNDS

(75) Inventor: Adam Meadows, Emeryville, CA (US)

(73) Assignee: Amyris Inc., Emeryville, CA (US)

(*) Notice: Subject to any disclaimer, the term of this patent is extended or adjusted under 35 U.S.C. 154(b) by 0 days.

(21) Appl. No.: 13/467,783

(22) Filed: May 9, 2012

(65) Prior Publication Data

US 2012/0288891 A1 Nov. 15, 2012

Related U.S. Application Data

(60) Provisional application No. 61/483,896, filed on May 9, 2011.

(51) Int. Cl.
| | |
|---|---|
| C12P 19/62 | (2006.01) |
| C12N 1/38 | (2006.01) |
| C12N 15/52 | (2006.01) |
| C12P 17/06 | (2006.01) |
| C12P 7/64 | (2006.01) |
| C12P 13/04 | (2006.01) |
| C12P 5/00 | (2006.01) |

(52) U.S. Cl.
CPC .......... *C12P 19/62* (2013.01); *C12N 1/38* (2013.01); *C12N 15/52* (2013.01); *C12P 5/007* (2013.01); *C12P 7/6409* (2013.01); *C12P 7/6427* (2013.01); *C12P 13/04* (2013.01); *C12P 17/06* (2013.01)

(58) Field of Classification Search
CPC .......... C12P 19/62; C12P 17/06; C12P 5/007; C12N 1/38
See application file for complete search history.

(56) References Cited

U.S. PATENT DOCUMENTS

| | | | |
|---|---|---|---|
| 7,285,402 B2 | 10/2007 | Gaddy et al. | |
| 7,901,924 B2 | 3/2011 | San et al. | |
| 8,143,035 B2 | 3/2012 | Lee et al. | |
| 8,241,888 B2 * | 8/2012 | Millis et al. | 435/254.2 |
| 2003/0092144 A1 * | 5/2003 | Millis et al. | 435/157 |

(Continued)

FOREIGN PATENT DOCUMENTS

| | | | | |
|---|---|---|---|---|
| EP | 2100963 A1 * | 9/2009 | | C12P 1/02 |
| WO | WO 00/01650 | * | 1/2000 | |

(Continued)

OTHER PUBLICATIONS

Guo et al., Protein tolerance to random amino acid change, 2004, Proc. Natl. Acad. Sci. USA 101: 9205-9210.*

(Continued)

*Primary Examiner* — Alexander Kim
(74) *Attorney, Agent, or Firm* — Morgan, Lewis & Bockius LLP

(57) ABSTRACT

The present disclosure relates to the use of pantothenate compounds as a non-genetic switch for the production of heterologous acetyl-CoA derived (HACD) compounds in microbial host cells. The invention provides genetically modified microorganisms that are more stable when stored and initially cultured under reduced pantothenate concentrations, cell culture media having reduced concentrations of pantothenate compounds, and methods of producing HACD compounds using the cell culture media and the genetically engineered microorganisms of the invention.

14 Claims, 9 Drawing Sheets

(56) References Cited

U.S. PATENT DOCUMENTS

| | | | |
|---|---|---|---|
| 2007/0238160 A1* | 10/2007 | Millis et al. | 435/252.33 |
| 2008/0213848 A1 | 9/2008 | Gaddy et al. | |
| 2009/0137014 A1* | 5/2009 | Tsuruta et al. | 435/157 |
| 2009/0186398 A1 | 7/2009 | San et al. | |
| 2010/0047885 A1 | 2/2010 | Lee et al. | |

FOREIGN PATENT DOCUMENTS

| | | | | |
|---|---|---|---|---|
| WO | WO/2008/039499 | * | 4/2008 | C12N 1/00 |
| WO | WO 2010/019696 | * | 2/2010 | C12Q 1/68 |

OTHER PUBLICATIONS

Lazar et al., Transforming Growth Factor α: Mutation of Aspartic Acid 47 and Leucine 48 Results in Different Biological Activity, 1988, Mol. Cell. Biol. 8:1247-1252.*

Hill et al., Functional Analysis of conserved Histidines in ADP-Glucose Pyrophosphorylase from *Escherichia coli*, 1998, Biochem. Biophys. Res. Comm. 244:573-577.*

Wacey et al., Disentangling the perturbational effects of amino acid substitutions in the DNA-binding domain of p53., Hum Genet, 1999, vol. 104, pp. 15-22.*

Pantoghenate ChemSpider (last viewed on Aug. 21, 2012).*

White et al., *Saccharomyces cerevisiae* Is Capable of de Novo Pantothenic Acid Biosynthesis Involving a Novel Pathway of β-Alanine Production from Spermine, The Journal of Biological Chemistry, (2001), vol. 276, pp. 10794-10800.*

Tamura et al., Production of Mevalonic Acid by Fermentation, Applied Microbiology, (1968), vol. 16, pp. 965-972.*

P76461 (last viewed on Aug. 23, 2012).*

Tripathi et al., High Yield Production of Heterologous Proteins with *Escherichia coli.*, Defence Science Journal., (2009) vol. 59, pp. 137-146.*

Azaman et al., Screening for the optimal induction parameters for periplasmic producing interferon-α2b *in Escherichia coli.*, African Journal of Biotechnology, (Sep. 20, 2010), vol. 9, pp. 6345-6354.*

Ning et al., Production of Recombinant Humanized Anti-HBsAgFab Fragment from Pichia pastoris by Fermentation, Journal of Biochemistry and Molecular Biology, (2005), vol. 38, pp. 294-299.*

Lynch, Michael, Evolution of the mutation rate., Trends in Genetics, (2010) vol. 26, pp. 345-352.*

Foods-high-in-VitB5 (last viewed on Sep. 5, 2013).*

Tullius et al. (A Replication-Limited Recombinant *Mycobacterium bovis* BCG Vaccine against Tuberculosis Designed for Human Immunodeficiency Virus-Positive Persons Is Safer and More Efficacious than BCG., Infect. Immun. (2008), vol. 76, No. 11, pp. 5200-5214.*

Hogenboom et al., Human mevalonate pyrophosphate decarboxylase is localized in the cytosol., Mol Genet Metab. (2004), vol. 81(3), pp. 216-224.*

P66927 (last viewed on Sep. 5, 2013).*

Chappell, Joseph., The biochemistry and Molecular Biology of Isoprenoid Metabolism., Plant Physiol. (1995), vol. 107, pp. 1-6.*

Dairi, Tohru., Studies on Biosynthetic Genes and Enzymes of Isoprenoids Produced by Actinomycetes., J. Antibiot., (2005) vol. 58(4), pp. 227-243.*

Fowler et al., Increased Malonyl coenzyme A Biosynthesis by Tuning the *Escherichia coli* Metabolic Network and Its Application to Flavanone Production., Applied and Environmental Microbiology (Sep. 2009), vol. 75, pp. 5831-5839.*

Barkovish et al., Metabolic Engineerign of Isoprenoids, Metabolic Engineering (2001), vol. 3, pp. 27-39.*

Paradise et al. Redirection of flux through the FPP branch-point in *Saccharomyces cerevisiae* by down-regulating squalene synthase., Biotechnology and Bioengineering (2008), vol. 100, Issue 2, pp. 371-378.*

Ro et al., Production of the antimalarial drug precursor artemisinic acid in engineered yeast., Nature (2006), vol. 440, pp. 940-943.*

Bacteria Growth (last viewed on Mar. 18, 2015).*

An et al., "Redirection of Carbon Flux to Lysine in a Recombinant of Corynebacterium lactofermentum ATCC 21799 by Limited Supply of Pantothenate," J. Bioscience and Bioengr., 1999, vol. 88(2), pp. 168-172.

Bernal et al., "Redirecting metabolic fluxes through cofactor engineering: Role of CoA-esters pool during L(−)-carnitie production by *Escherichia coli*," J. Biotech., 2007, vol. 132, pp. 110-117.

Lin et al., "Increasing the Acetyl-CoA Pool in the Presnece of Overexpressed Phosphoenolpyruvae Carboxylase or Pyruvate Carboxylase Enhances Succinate Production in *Escherichia coli*," Biotechnol., 2004, vol. 20, pp. 1599-1604.

San et al., "Metabolic Engineering through Cofactor Manipulation and Its Effects on Metabolic Flux Redistribution in *Escherichia coli*," Metabolic Engr., 2002, vol. 4, pp. 182-192.

Vadali et al., "Applicability of CoA/acetyl-CoA manipulation system to enhance isoamyl acetate production in *Escherichia coli*," Metabolic Engr., 2004, vol. 6, pp. 294-299.

Vadali et al., "Cofactor engineering of intracellular CoA/acetyl-CoA and its effect on metabolic flux redistribution in *Escherichia coli*," Metabolic Engr., 2004, vol. 6, pp. 133-139.

Vadali et al., "Enhanced Lycopene Productivity by Manipulation of Carbon Flow to Isopentenyl Diphosphae in *Escherichia coli*," Biotechnol., 2005, vol. 21, pp. 1558-1561.

International Search Report for PCT Application No. PCT/US12/37127, mailed on Jul. 24, 2012, 4 pages.

Written Opinion for PCT Application No. PCT/US12/37127, mailed on Jul. 24, 2012, 5 pages.

ISA/US, PCT International Search Report dated Jul. 24, 2012 for International Application No. PCT/US12/37127.

Taherzadeh et al: "The effects of pantothenate deficiency and acetate addition on anaerobic batch fermentation of glucose by *Saccharomyces cerevisiae*". Applied Microbiology and Biotechnology. vol. 46. 1996. pp. 176-182.

Olzhausen et al: "Genetic analysis of 1-15 coenzyme A biosynthesis in the yeast *Saccharomyces cerevisiae*: identification of a conditional mutation in the pantothenate kinase gene CAB1", Current Genetics. vol. 55. 2009. pp. 163-173.

MacWilliams, et al. "Luria Broth (LB) and Luria Agar (LA) Media and Their Uses Protocol", Jul. 22, 2013, 6 pages.

Cold Spring Harbor Protocols, WesternBright™,"Yeast extract-peptone-dextrose growth medium (YEPD)", 1 page.

Biotech Solabia Group, "Yeast Extract-A1202", Jun. 30, 2008, 2 pages.

* cited by examiner

US 9,670,518 B2

PRODUCTION OF ACETYL-COENZYME A DERIVED COMPOUNDS

1. CROSS REFERENCE TO RELATED APPLICATION

This application claims priority to U.S. Provisional Patent Application No. 61/483,896, filed May 9, 2011, which is incorporated herein by reference.

2. TECHNICAL FIELD

The present disclosure relates to the use of pantothenate (also known as vitamin B5) as a non-genetic switch for modulating the production of a heterologous acetyl-CoA derived compounds by a genetically modified host cell.

3. BACKGROUND OF THE INVENTION

The advent of synthetic biology has brought about the promise of fermentative microbial production of biofuels, chemicals and biomaterials from renewable sources at industrial scale and quality. For example, functional non-native biological pathways have been successfully constructed in microbial hosts for the production of precursors to the antimalarial drug artemisinin (see, e.g., Martin et al., *Nat Biotechnol* 21:796-802 (2003); fatty acid derives fuels and chemicals (e.g., fatty esters, fatty alcohols and waxes; see, e.g., Steen et al., *Nature* 463:559-562 (2010); polyketide synthases that make cholesterol lowering drugs (see, e.g., Ma et al., *Science* 326:589-592 (2009); and polyketides (see, e.g., Kodumal, *Proc Natl Acad Sci USA* 101:15573-15578 (2004). However, the commercial success of synthetic biology will depend largely on whether the production cost of renewable products can be made to compete with, or outcompete, the production costs of their respective non-renewable counterparts.

Strain stability can be a major driver of the cost of industrial fermentations, as it affects the length of time that a continuous fermentation can be run productively. Strain stability generally refers to the ability of a microbe to maintain favorable production characteristics (i.e., high yield (grams of compound per gram of substrate) and productivity (grams per liter of fermentation broth per hour)) of a non-catabolic fermentation product over extended cultivation times. In particular, genetic stability, which is the propensity of the producing microbial population to have little to no alteration of the intended allelic frequency of genes relevant to the production of product over time, plays a major role in the sustained output of product.

For non-catabolic fermentation of products other than biomass (which products, by definition, consume metabolic energy and carbon that could otherwise be used in the production of more cells), the basis of instability is two-fold: evolutionary mutation and selection. First, loss-of-production mutations arise spontaneously and randomly. Second, a growth rate or "fitness" advantage of cells with reduced product yields leads to an eventual population sweep by low producers, and thereby decreases the overall culture performance. This phenomenon can be referred to as "strain degeneration."

Brazilian fuel ethanol fermentations achieve extremely high yields of ethanol from sugar for long periods of time, i.e., about 90% of maximum theoretical yield. This is in part because the production of ethanol is catabolic: it generates 2 ATP per molecule of sugar produced and is redox balanced without the involvement of oxygen. A cell that mutates to not produce ethanol is less fit under the low oxygen conditions of the fermentor and will not sweep the population. This allows industrial ethanol fermentations to recycle the majority of yeast biomass throughout the season, thereby minimizing conversion of sugar into yeast cell biomass and directing nearly all of the sugar to ethanol production. This extended propagation and re-use of biomass increases the efficiencies of ethanol production: operational expenditures are reduced because less sugar goes to biomass during each cycle (i.e., the yield increases); and capital expenditures are reduced because fewer and smaller fermentors are needed to build biomass for inoculations.

By contrast, the production of many acetyl-CoA derived hydrocarbons (e.g., isoprenoids, fatty acids, and polyketides) are generally non-catabolic in nature; they usually require a net input of ATP, NADPH, and carbon, often with large amounts of oxygen supplied to help balance the redox of the system. Such an environment makes evolution towards lower product, higher biomass yielding genotypes more favorable, and leads to a higher rate of strain degeneration.

One way to decrease the negative selective pressure of producing non-catabolic products is to switch off the formation of product during periods where the product is not desired, such as during phases of the fermentation where biomass must be generated in order to maximize fermentor productivity. Genetic switches are a common way of achieving this in practice, but may have disadvantages due to, for example, the cost of an exogenous inducer, the delay in transcribing and translating the switch, and may also be a source of low producers if mutations occur in the genetic switch itself. However, a metabolic switch does not suffer from these disadvantages.

Thus, there is a need in the art for metabolic switches that can control the timing of production of acetyl-CoA derived compounds during fermentation.

4. SUMMARY OF THE INVENTION

Provided herein is a fermentation process for producing a heterologous acetyl-CoA derived compound ("HACD compound") from a genetically modified host cell. In some embodiments, the process comprises two phases: a build stage during which HACD compound production is substantially reduced (the "off" stage) while cell biomass is accumulated; and a production phase, during which HACD compound production is turned on. Thus, the negative selective pressure associated with HACD compound production is alleviated during a stage of fermentation in which production is not needed. Without being bound by theory, it is believed that reduction or elimination of the HACD compound production during the build stage results in improved stability of the strain during the production stage, resulting in longer sustained HACD compound production, thereby increasing the overall yield and/or productivity of the strain. The "off" and "on" states of HACD compound production in the fermentation culture is controlled by the amount of a precursor to acetyl-CoA, pantothenate, in the culture medium.

Acetyl-CoA is the activated form of acetate that is used as a building block for many important biomolecules, including amino acids, fatty acids, isoprenoids, and polyketides. The cofactor, coenzyme A (the CoA portion of acetyl-CoA) is biosynthesized from three precursors (FIG. 1B). Two of these precursors, namely L-cysteine and adenosine-5'-triphosphate, can be efficiently synthesized by most living systems and thus are not limiting. In contrast, the third precursor, pantothenate is limiting and only produced by most living systems in insufficient quantities. As a result, most living systems require external sources of a pantothenate compound (e.g., in the culture medium or a food source) for optimal growth, health and viability. However, the methods provided herein are based in part on the unexpected discovery that pantothenate can be used in limited amounts or omitted entirely when culturing cells engineered to produce acetyl-CoA derived compounds. These cells can maintain growth and viability, and in some cases, demonstrate improved growth, under limiting pantothenate concentrations. Advantageously, these same conditions result in a reduction in the production of the HACD compound. Accordingly, the methods provided herein utilize pantothenate as a non-genetic switch to effect the "off" and "on" stages of an improved fermentation process for production of heterologous acetyl-CoA derived compounds.

Thus, in one aspect, provided herein is a method of producing a heterologous acetyl-CoA derived (HACD) compound in a host cell comprising:
(a) culturing a population of genetically modified host cells capable of producing an HACD compound in a culture medium comprising a carbon source and a limiting amount of pantothenate, wherein the limiting amount of pantothenate limits the production of the HACD compound by the host cell; followed by
(b) culturing said population or a subpopulation thereof in a culture medium comprising a carbon source and a non-limiting amount of pantothenate, wherein the non-limiting amount of pantothenate is an amount greater than the limiting amount of pantothenate, wherein said population or subpopulation thereof produces a greater amount of the HACD compound in the presence of the non-limiting amount of pantothenate.

In some embodiments, the limiting amount of pantothenate is determined by performing a pantothenate titration, wherein the host cells are cultured in a growth medium comprising increasing concentrations of pantothenate, and HACD compound production is determined at each concentration of pantothenate, wherein the pantothenate titration comprises saturating amounts of pantothenate whereby HACD compound production is at its maximum; wherein the limiting amount of pantothenate is any concentration of pantothenate at which HACD compound production is less than at its maximum.

In some embodiments, production of the HACD compound during the "build" stage (step (a)) is less than 50, 40, 30, 20 or 10% of the maximum HACD compound production of the genetically modified host cell. In some embodiments, production of the HACD compound during the "production" stage (step (b)) is greater than 50, 60, 70, 80 or 90% of the maximum HACD compound production of the genetically modified host cell.

In some embodiments, the culturing of step (a) is for a period of time sufficient for said population to reach a cell density ($OD_{600}$) of between 0.01 and 400. In some embodiments, the culturing of step (b) is for a period of 3 to 20 days. In some embodiments, the limiting amount of pantothenate is below 0.2 mg/L. In some embodiments, the limiting amount of pantothenate is 0 mg/L. In some embodiments, the non-limiting amount of pantothenate is above 0.2 mg/L. In some embodiments, the non-limiting amount of pantothenate is at least the minimum pantothenate concentration at which HACD compound production is at its maximum. In some embodiments, the non-limiting amount of pantothenate is 10 mg/L.

In some embodiments, step (b) comprises adding pantothenate to culture medium comprising the limiting amount of pantothenate until the medium comprises a non-limiting amount of pantothenate. In some embodiments, step (b) comprises transferring the population of step (a) to a new culture medium comprising a non-limiting amount of pantothenate.

In some embodiments, the methods provided herein result in increased production of the HACD compound by the population of genetically modified host cells, compared to production resulting from a method not comprising culturing the cells in a limiting amount of pantothenate. In some embodiments, production of the HACD compound is measured in terms of yield (gram of HACD compound produced per gram of carbon substrate) or productivity (grams of HACD compound produced per liter of culture medium per hour). In some embodiments, the methods further comprising recovering the HACD compound.

In some embodiments, the pantothenate is (R)-pantothenate or any salt thereof. In some embodiments, the host cell is selected from the group consisting of a fungal cell, a bacterial cell, a plant cell, and an animal cell. In some embodiments, the host cell is a yeast cell. In some embodiments, the HACD compound is selected from the group consisting of an amino acid, a fatty acid, an isoprenoid, and a polyketide.

In some embodiments, the host cell is capable of producing an isoprenoid and comprises at least one heterologous nucleic acid encoding an isoprenoid pathway enzyme selected from the group consisting of:
  a) an enzyme that condenses two molecules of acetyl-coenzyme A to form acetoacetyl-CoA;
  b) an enzyme that condenses acetoacetyl-CoA with another molecule of acetyl-CoA to form 3-hydroxy-3-methylglutaryl-CoA (HMG-CoA);
  c) an enzyme that converts HMG-CoA into mevalonate;
  d) an enzyme that converts mevalonate into mevalonate 5-phosphate;
  e) an enzyme that converts mevalonate 5-phosphate into mevalonate 5-pyrophosphate;
  f) an enzyme that converts mevalonate 5-pyrophosphate into IPP;
  g) an enzyme that converts IPP into DMAPP;
  h) a polyprenyl synthase that can condense IPP and/or DMAPP molecules to form polyprenyl compounds containing more than five carbons;
  i) an enzyme that condenses IPP with DMAPP to form GPP;
  j) an enzyme that condenses two molecules of IPP with one molecule of DMAPP;
  k) an enzyme that condenses IPP with GPP to form FPP;
  l) an enzyme that condenses IPP and DMAPP to form GGPP; and,
  m) an enzyme that condenses IPP and FPP to form GGPP.

In some embodiments, the host cell further comprises a heterologous nucleic acid encoding an enzyme that modifies a polyprenyl, selected from the group consisting of a geraniol synthase, a linalool synthase, a limonene synthase, a myrcene synthase, an ocimene synthase, an α-pinene synthase, β-pinene synthase, a sabinene synthase, a γ-terpinene synthase, a terpinolene synthase, an amorphadiene synthase, an α-farnesene synthase, a β-farnesene synthase, a farnesol synthase, a nerolidol synthase, a patchoulol synthase, a nootkatone synthase, an abietadiene synthase.

In some embodiments, the host cell is capable of producing a polyketide and comprises at least one heterologous nucleic acid encoding a polyketide synthesis enzyme, wherein the polyketide synthesis enzyme is selected from the group consisting of:
- a) an enzyme that condenses at least one of acetyl-CoA and malonyl-CoA with an acyl carrier protein;
- b) an enzyme that condenses a first reactant selected from the group consisting of acetyl-CoA and malonyl-CoA with a second reactant selected from the group consisting of malonyl-CoA or methylmalonyl-CoA to form a polyketide product;
- c) an enzyme that reduces a β-keto chemical group on a polyketide compound to a β-hydroxy group;
- d) an enzyme that dehydrates an alkane chemical group in a polyketide compound to produce an α-β-unsaturated alkene;
- e) an enzyme that reduces an α-β-double-bond in a polyketide compound to a saturated alkane; and,
- f) an enzyme that hydrolyzes a polyketide compound from an acyl carrier protein.

In some embodiments, the polyketide is a lipid having at least one of antibiotic, antifungal, and antitumor activity. In some embodiments, the polyketide is selected from the group consisting of a macrolid, an antibiotic, an antifungal, a cytostatic compound, an anticholesterolemic compound, an antiparasitic compound, a coccidiostatic compound, an animal growth promoter and an insecticide.

In some embodiments, the host cell is capable of producing a fatty acid and comprises at least one heterologous nucleic acid encoding a fatty acid synthesis enzyme, wherein the fatty acid synthesis enzyme is selected from the group consisting of:
- a) an enzyme that covalently links at least one of acetyl-CoA and malonyl-CoA to an acyl carrier protein (ACP);
- b) an enzyme that condenses acetyl-ACP and malonyl-ACP to form acetoacetyl-ACP;
- c) reduce the double bond in acetoacetyl-ACP with NADPH to form a hydroxyl group in D-3-hydroxybutyryl hydroxylase-ACP;
- d) an enzyme that dehydrates D-3-Hydroxybutyryl hydroxylase-ACP to create a double bond between the beta- and gamma-carbons forming crotonyl-ACP;
- e) an enzyme that reduces crotonyl ACP with NADPH to form butyryl-ACP; and,
- f) an enzyme that hydrolyzes a C16 acyl compound from an acyl carrier protein to form palmitate.

In some embodiments, the fatty acid is selected from the group consisting of palmitate, palmitoyl CoA, palmitoleic acid, sapienic acid, oleic acid, linoleic acid, α-linolenic acid, arachidonic acid, eicosapentaenoic acid, erucic acid, and docosahexaenoic acid.

In another aspect, provided herein is a method of producing a heterologous acetyl-CoA derived (HACD) compound in a host cell comprising:
- (a) culturing a population of genetically modified host cells capable of producing an HACD compound in a culture medium comprising a carbon source and lacking pantothenate supplementation; followed by
- (b) culturing said population or a subpopulation thereof in a culture medium comprising a carbon source and supplemented with at least 1 mg/L pantothenate.

In some embodiments, the culturing of step (a) is for a period of time sufficient for said population to reach a cell density ($OD_{600}$) of between 0.01 and 400. In some embodiments, the culturing of step (b) is for a period of 3 to 20 days.

5. BRIEF DESCRIPTION OF FIGURES

Figure 1:
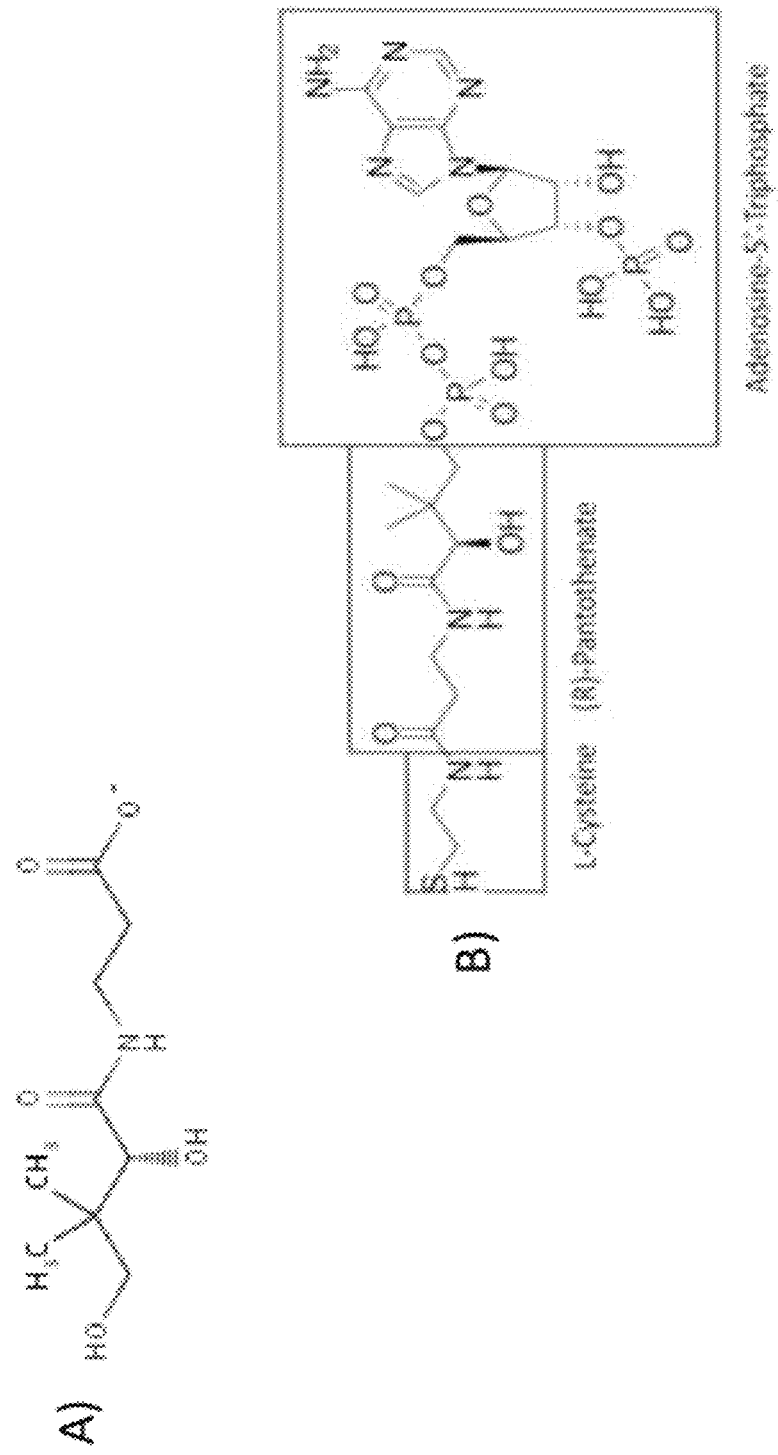
FIG. 1 shows the molecular structures of (A) R-pantothenate, and (B) coenzyme A, with highlighting of the three segments of coenzyme A that are derived from its three precursors: L-cysteine, (R)-pantothenate, and ATP.
Figure 2:
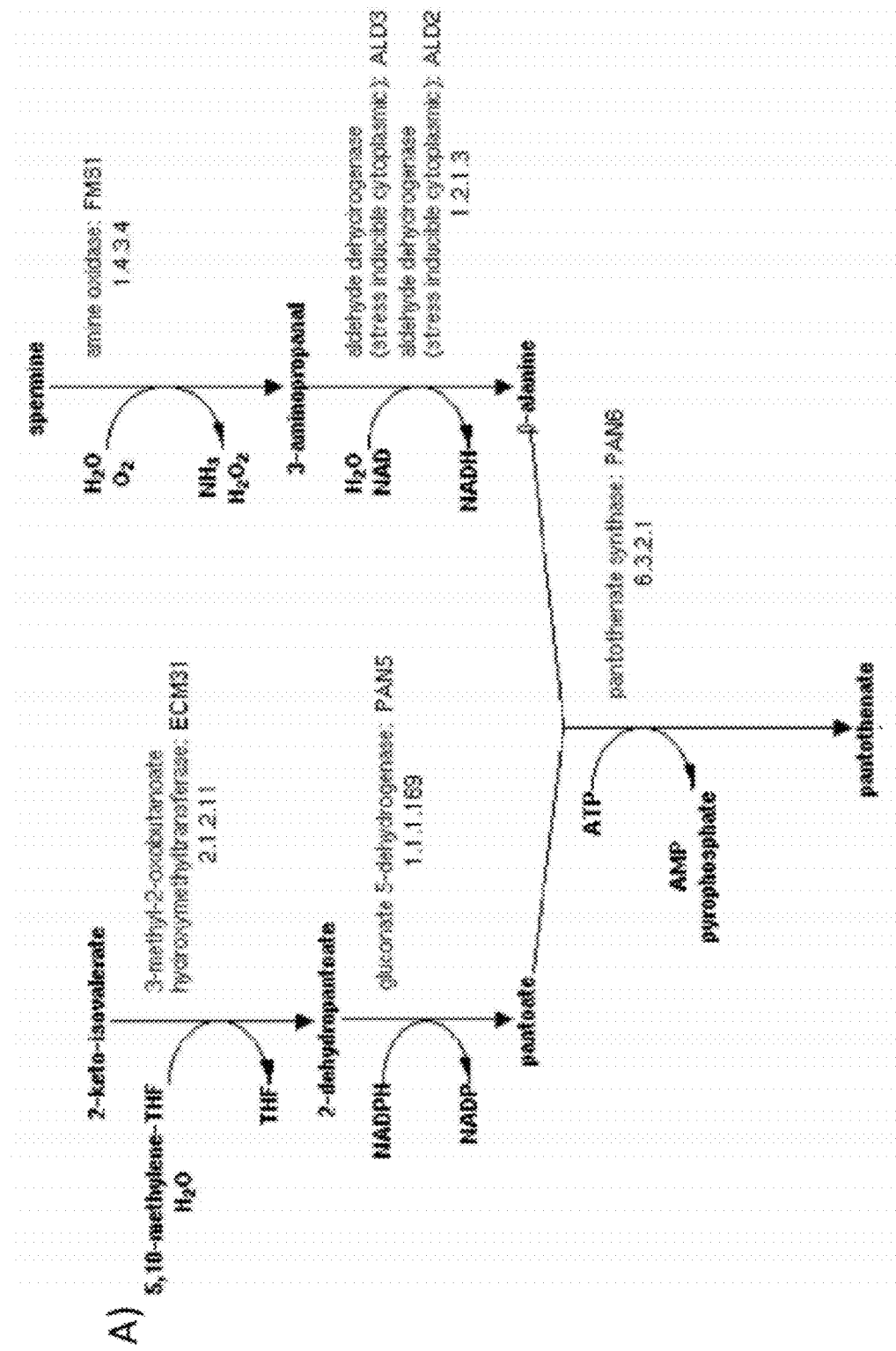
FIG. 2 shows the pantothenate biosynthetic pathway in yeast (A) and bacteria (B).
Figure 2:
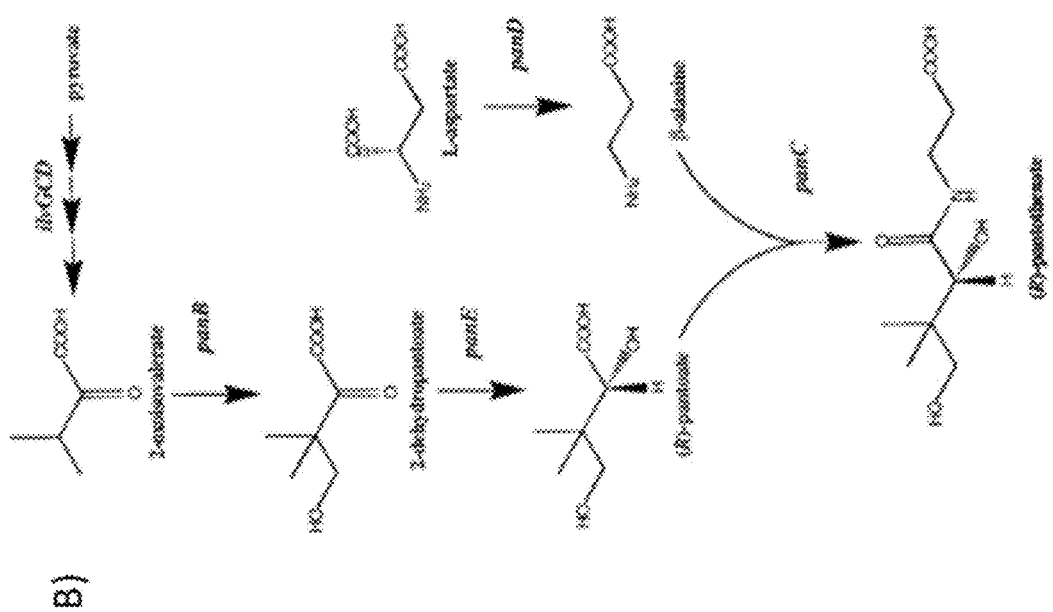
Figure 3:
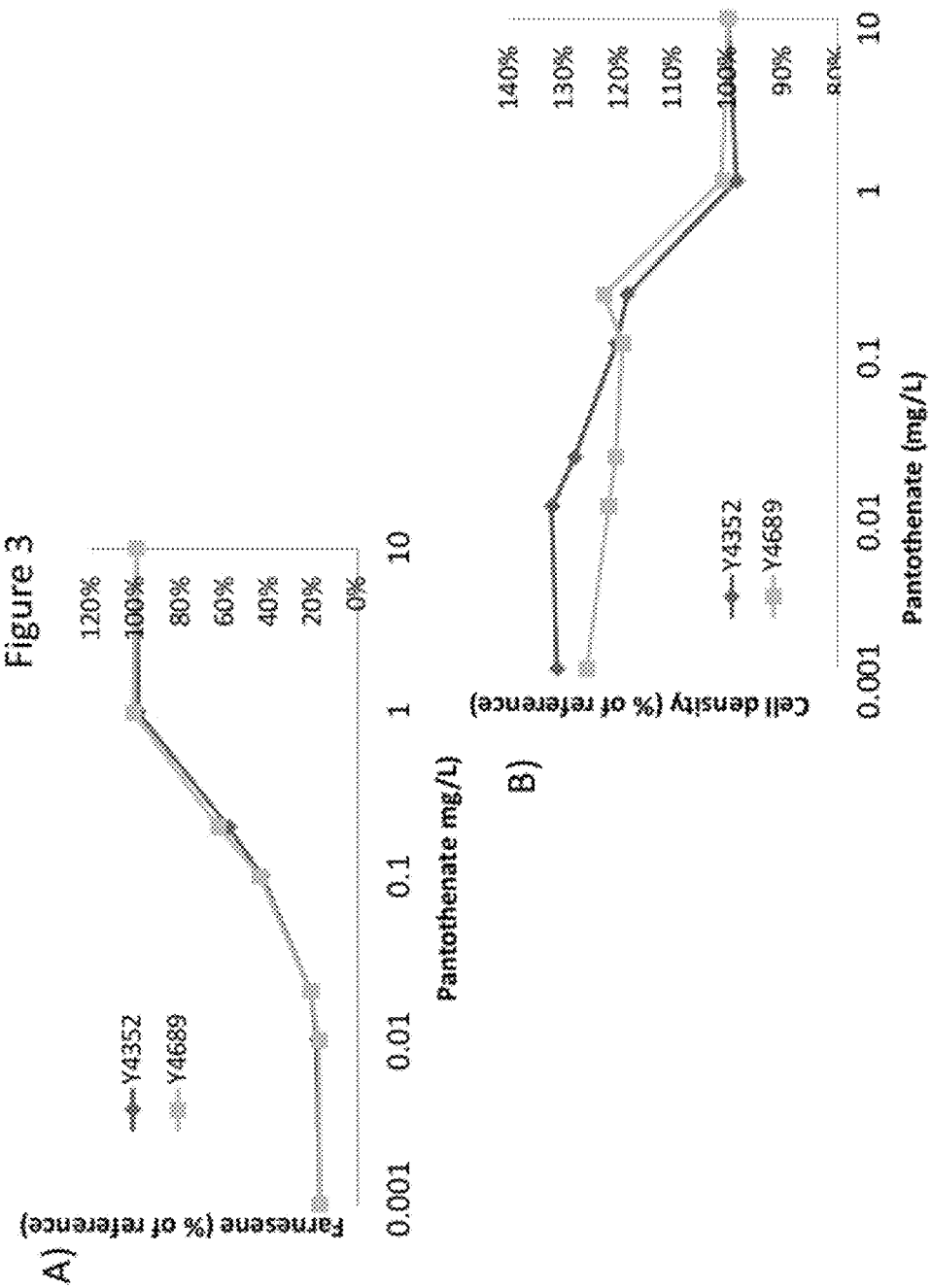

FIG. 3 shows yields of an exemplary HACD compound (A) and cell densities (B) obtained for strains Y4689 and Y4352 in the presence of various amounts of pantothenate. Strains Y4689 and Y4352 each comprised heterologous enzymes (including the enzymes of the MEV pathway: IPP isomerase, FPP synthase, and farnesene synthase) and were capable of producing HACD compound at yields of 15% and 13%, respectively.

Figure 4:
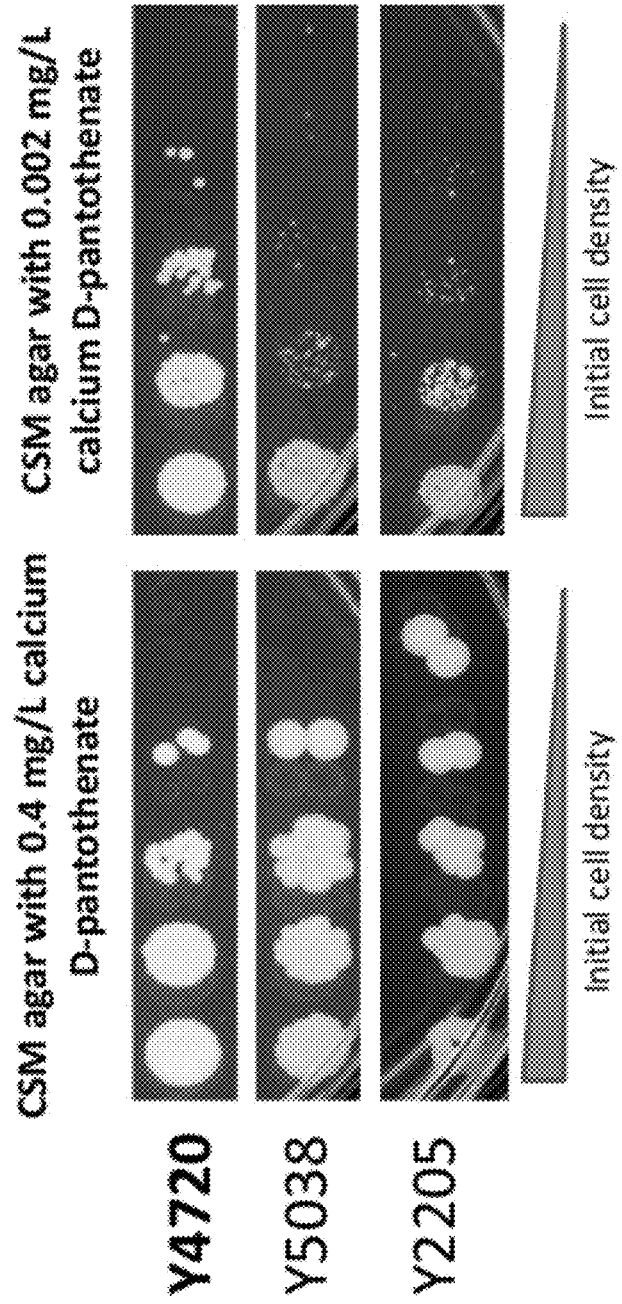

FIG. 4 shows cell growth on agar comprising 0.4 mg/L or 0.002 mg/L of pantothenate of strains Y4720, Y5038, and Y2205. Strains Y4720 and Y5038 each comprised heterologous enzymes (including the enzymes of the MEV pathway: IPP isomerase, FPP synthase, and farnesene synthase) and were capable of producing an exemplary HACD compound at yields of 14% and 6%, respectively. Strain Y2205 was a CEN.PK2 wild-type control that did not produce any HACD compound.

Figure 5:
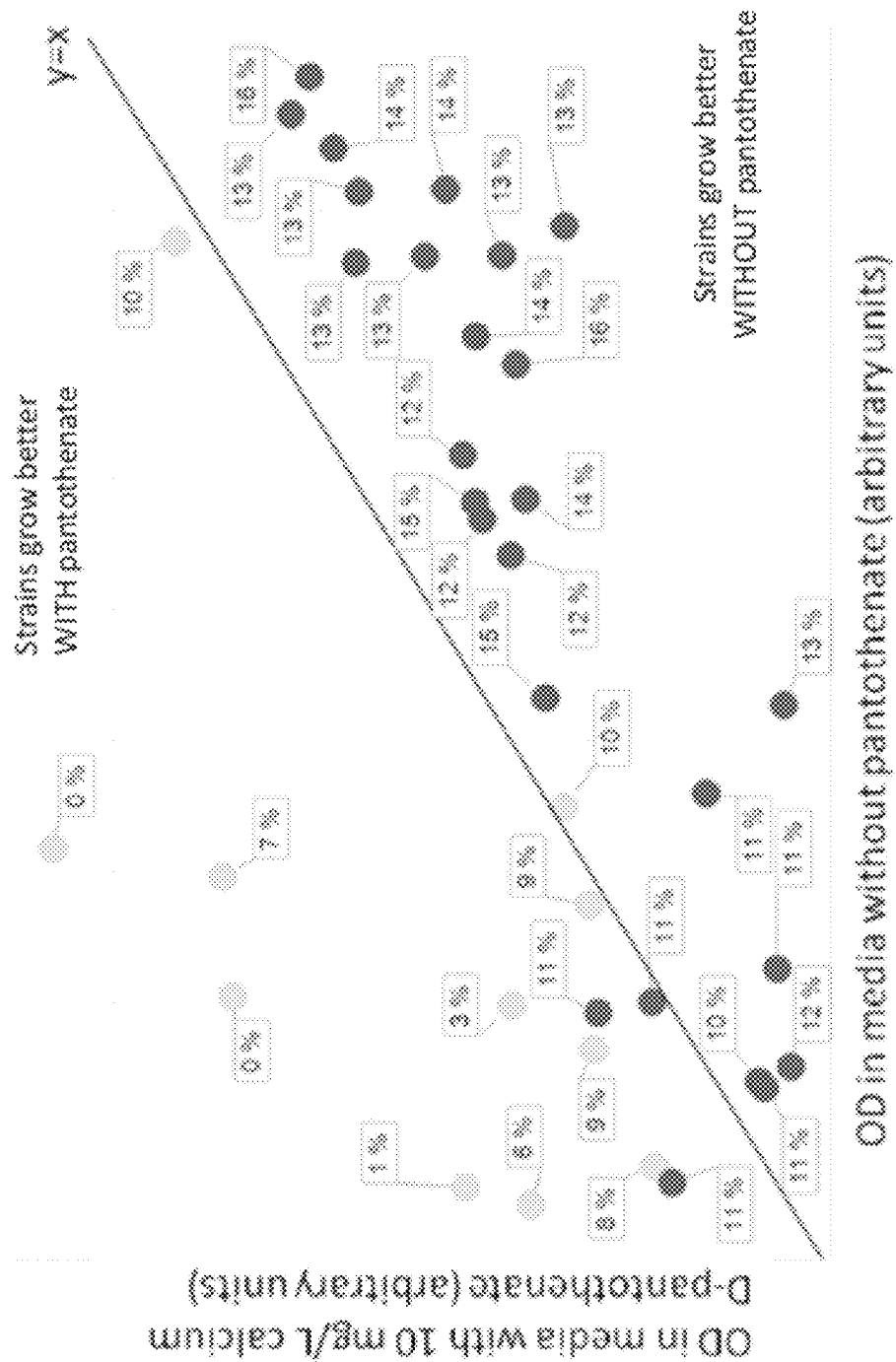

FIG. 5 shows cell growth of yeast host cells capable of producing varying yields of the exemplary HACD compound, farnesene, in the presence of 0 or 10 mg/L of pantothenate. Approximate farnesene yield of each strain is indicated, and data points for strains that produce farnesene at a yield of less than 10% are gray whereas data points for strains that produce farnesene at a yield of 10% or more are black.

Figure 6:
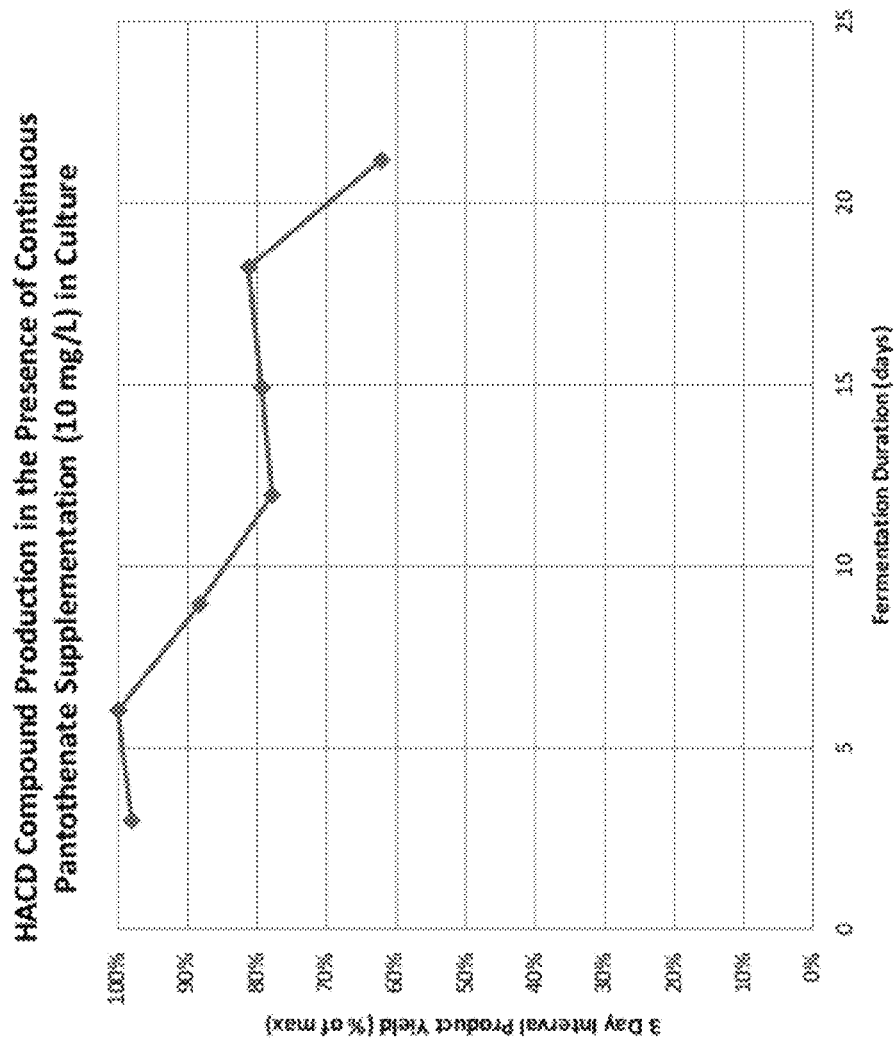

FIG. 6 shows strain degeneration (i.e., decline of HACD compound production over time) of a population of yeast host cells capable of producing an HACD compound, farnesene, in the presence of 10 mg/L of pantothenate.

Figure 7:
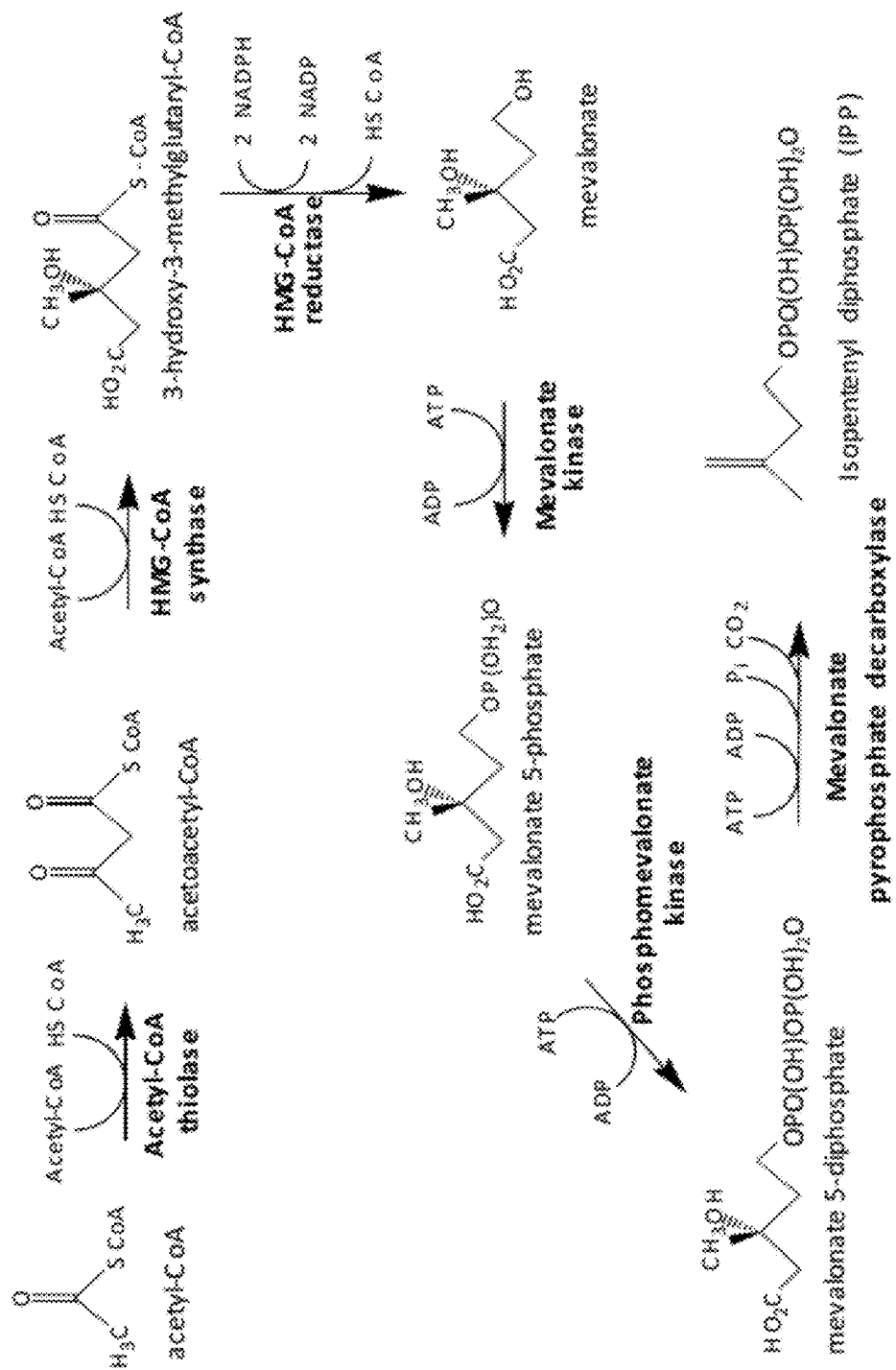

FIG. 7 provides a schematic representation of the mevalonate ("MEV") pathway for the production of isopentenyl diphosphate ("IPP").

Figure 8:
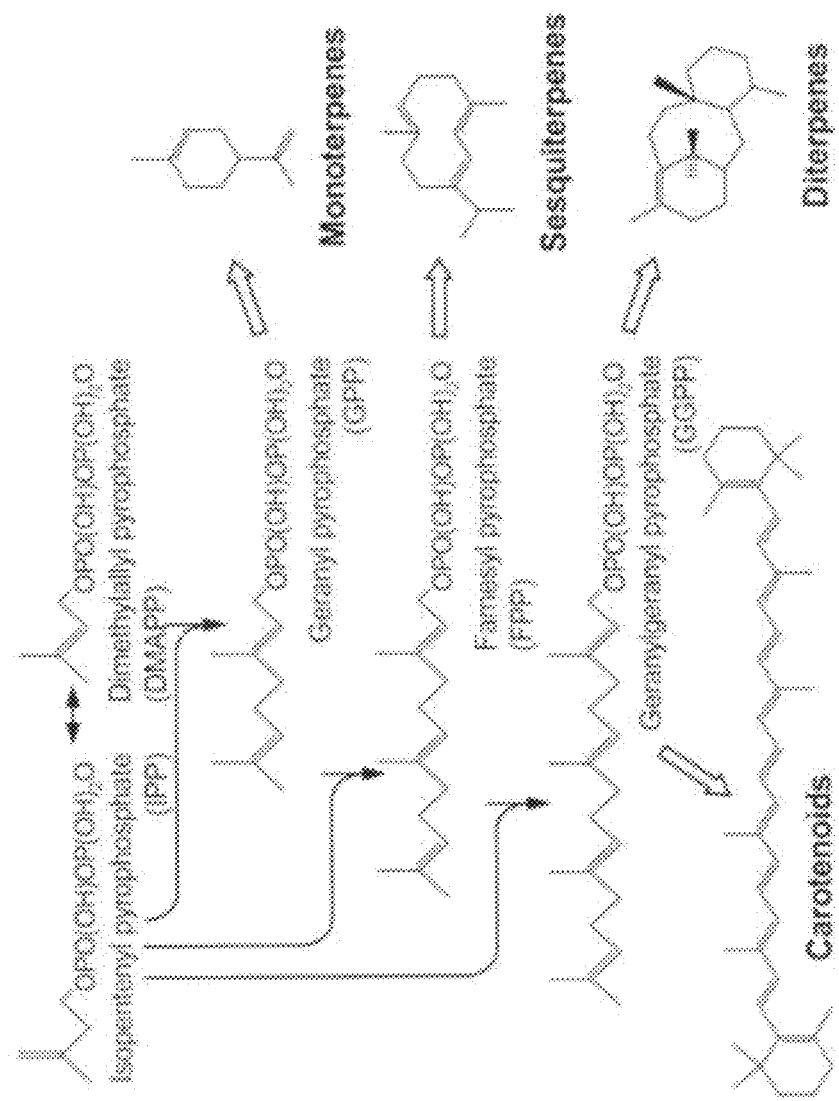

FIG. 8 provides a schematic representation of the conversion of IPP and dimethylallyl pyrophosphate ("DMAPP") to geranyl pyrophosphate ("GPP"), farnesyl pyrophosphate ("FPP"), and geranylgeranyl pyrophosphate ("GGPP").

6. DESCRIPTION OF EMBODIMENTS

6.1 Definitions

The term "acetyl-CoA derived compound" refers to a molecule that is biosynthesized by a host cell from one or more acetyl groups derived from acetyl-CoA.

The term "endogenous" refers to a substance or process that can occur naturally in a host cell.

The term "genetically modified" denotes a host cell that comprises a heterologous nucleotide sequence.

The term "HACD compound" refers to the heterologous acetyl-CoA derived compound that is produced by the genetically modified host cells. HACD compounds include but are not limited to amino acids, fatty acids, isoprenoids, and polyketides. In some embodiments, the HACD compound is selected from the group consisting of isoprenoids, fatty acids and polyketides.

The term "heterologous" refers to what is not normally found in nature. The term "heterologous compound" refers to the production of a compound by a cell that does not normally produce the compound, or to the production of a compound at a level at which it is not normally produced by the cell.

The term "heterologous enzyme" refers to an enzyme that is not normally found in a given cell in nature. The term encompasses an enzyme that is:

(a) exogenous to a given cell (i.e., encoded by a nucleotide sequence that is not naturally present in the host cell or not naturally present in a given context in the host cell); and (b) naturally found in the host cell (e.g., the enzyme is encoded by a nucleotide sequence that is endogenous to the cell) but that is produced in an unnatural amount (e.g., greater or lesser than that naturally found) in the host cell.

The term "production" generally refers to an amount of HACD compound produced by a genetically modified host cell provided herein. In some embodiments, production is expressed as a yield of the HACD compound by the host cell. In other embodiments, production is expressed as a productivity of the host cell in producing the HACD compound.

The term "productivity" refers to production of an HACD compound by a host cell, expressed as the amount of HACD compound produced (by weight) per amount of fermentation broth in which the host cell is cultured (by volume) over time (per hour).

The term "yield" refers to production of an HACD compound by a host cell, expressed as the amount of HACD compound produced per amount of carbon source consumed by the host cell, by weight.

6.2 Use of Pantothenate as a Non-Genetic Switch for Modulating the Production of Heterologous Compounds The methods and compositions provided herein are based on the discovery that when pantothenate is limited or omitted from culture medium in which genetically modified host cells capable of producing HACD compounds are cultured, HACD compound production is substantially reduced; and when pantothenate is provided in the culture medium, HACD compound production is increased. Thus, pantothenate can act as a non-genetic switch for the production of HACD compounds in genetically modified host cells. In particular, controlling the timing of HACD compound production to occur only when production is desired redirects the carbon flux during the non-production phase into cell maintenance and biomass. This more efficient use of carbon greatly reduces the metabolic burden on the host cells, increases the stability of the heterologous genes, reduces strain degeneration, and contributes to better overall health and viability of the cells. Accordingly, the methods provided herein utilize pantothenate as a non-genetic switch to effect the "off" and "on" stages of an improved fermentation process for production of heterologous acetyl-CoA derived compounds.

Thus, in one aspect, provided herein is a method of producing a heterologous acetyl-CoA derived (HACD) compound in a host cell comprising:

(a) culturing a population of genetically modified host cells capable of producing an HACD compound in a culture medium comprising a carbon source and a limiting amount of pantothenate, wherein the limiting amount of pantothenate limits the production of the HACD compound by the host cell; followed by (b) culturing said population or a subpopulation thereof in a culture medium comprising a carbon source and a non-limiting amount of pantothenate, wherein the non-limiting amount of pantothenate is an amount greater than the limiting amount of pantothenate, wherein said population or subpopulation thereof produces a greater amount of the HACD compound in the presence of the non-limiting amount of pantothenate.

In the first step (i.e., the "build" stage, step (a)), the genetically modified host cells are grown in a growth or "build" medium in which pantothenate is limited or omitted. In the second step (i.e., the "production" stage, step (b)), a pantothenate compound is added to the culture medium, which serves as a non-genetic switch to substantially boost the production of the HACD compound. The initial growth at low or absent pantothenate levels ensures that the energy requirements of the cells are met while the biomass of the cells quickly increases. Thereafter, switching to a growth medium containing a pantothenate compound enables the synthesis of the HACD product.

Example 5 (below) and FIG. 3A illustrates the effect of pantothenate compound concentration in the culture medium on HACD compound production in a genetically modified host cell having a high metabolic flux through the acetyl-CoA biosynthesis pathway to produce the isoprenoid farnesene. At low pantothenate compound levels (0.2 mg/L, <1% of the maximum pantothenate compound concentration tested), there is virtually no production of the HACD compound. Increasing the pantothenate compound levels correlates with increased HACD compound production until the effect plateaus. Further increases beyond 1 mg/L pantothenate (10% of the maximum pantothenate compound concentration tested) results in no further increases in HACD compound production.

Notably, the growth of these cells shows the opposite trend to HACD compound production. FIG. 3B illustrates the growth of the same strains at the same pantothenate concentration levels that were tested for HACD compound production. Absent or low levels of a pantothenate compound actually result in better growth than that observed when the strains were cultured at pantothenate levels that are required for maximum HACD compound production. This response to low pantothenate levels was more frequently observed among host cells engineered to produce higher amounts of an HACD compound, as illustrated by Examples 6 and 7 and FIGS. 4 and 5 below. Thus, in certain strains capable of producing HACD compounds, a further benefit of improved growth is observed when cultured in little or no pantothenate. Improved growth during the "build" stage (i.e., when HACD compound production is turned off) allows for a faster buildup of the cell biomass needed for the production phase of the fermentation.

Example 8 and FIG. 6, provided below, demonstrates the phenomenon of strain degeneration, which can occur when pantothenate is provided throughout all stages of a fermentation process. Robust production of the HACD farnesene is transiently maintained at the outset of fermentation, but over time, production is reduced to close to only 60% of the maximum production previously observed. This results in an overall decreased production (e.g., yield and/or productivity) of the host cell population. However, as described in Example 9 and Table 1 below, by limiting or omitting pantothenate from the culture medium during the "build" stage, HACD compound production can be substantially increased over the course of the fermentation.

6.2.1 Limiting and Non-Limiting Amounts of Pantothenate

In some embodiments of the methods provided herein, a "limiting" and "non-limiting" amount of pantothenate for use in the methods provided herein can be determined for any genetically modified host cell capable of producing an HACD compound. In some embodiments, a non-limiting amount of pantothenate is determined by performing an HACD compound production curve in the presence of increasing amounts of pantothenate in the culture medium, i.e., a pantothenate titration. An exemplary pantothenate titration is provided in Example 5 and FIG. 3 below.

For example, a population of genetically modified host cells may be divided into a plurality of subpopulations and cultured in parallel, wherein each subpopulation is grown in culture media comprising a different, e.g., increasing amount of pantothenate (including no pantothenate), and HACD compound production is assayed after a defined period of time. In preferred embodiments, the pantothenate titration comprises at least two concentrations of pantothenate whereby HACD compound production of the host cells is plateaued at a maximum amount, that is, where no further increase in HACD compound production is observed with an increase in pantothenate concentration. In some embodiments, a "non-limiting amount" of pantothenate is at least the minimum amount of pantothenate at which HACD compound production of the host cells is plateaued at its maximum. This amount can also be referred to as a "saturating" or "optimal" amount of pantothenate for HACD compound production for the particular host cell, whereby the amount does not limit the HACD compound production of the host cell, that is, where HACD compound production is not negatively impacted due to a lack of pantothenate in the culture medium. In other embodiments, the "non-limiting" amount of pantothenate can include any concentration of pantothenate at which HACD compound production is observed, even where HACD compound production is suboptimal.

Once a non-limiting amount of pantothenate has been determined for the host cell, this amount may be used during the production stage of the fermentation process, and can also be used to determine a "limiting" amount of pantothenate to be used during the build stage. In some embodiments, a "limiting" amount of pantothenate can be any amount below a non-limiting amount of pantothenate, for use in the build stage of the fermentation.

In some embodiments, the non-limiting amount of pantothenate is at least 0.01 mg/L (weight pantothenate per volume of culture medium). In some embodiments, the non-limiting amount of pantothenate is at least 0.1 mg/L. In some embodiments, the non-limiting amount of pantothenate is at least 1 mg/L. In some embodiments, the non-limiting amount of pantothenate is at least 10 mg/L. In some embodiments, the non-limiting amount of pantothenate is an amount of pantothenate between 0.01 mg/L and 10 mg/L. In some embodiments, the non-limiting amount of pantothenate is an amount of pantothenate between 0.01 mg/L and 1 mg/L. In some embodiments, the non-limiting amount of pantothenate is an amount of pantothenate between 0.01 mg/L and 0.1 mg/L. In some embodiments, the non-limiting amount of pantothenate is an amount of pantothenate between 1 mg/L and 10 mg/L. In some embodiments, the non-limiting amount of pantothenate is an amount above 0.001 mg/L. In some embodiments, the non-limiting amount of pantothenate is an amount above 0.01 mg/L. In some embodiments, the non-limiting amount of pantothenate is an amount above 0.02 mg/L. In some embodiments, the non-limiting amount of pantothenate is an amount above 0.1 mg/L. In some embodiments, the non-limiting amount of pantothenate is an amount above 0.2 mg/L. In some embodiments, the non-limiting amount of pantothenate is an amount above 1 mg/L. In some embodiments, the non-limiting amount of pantothenate is an amount above 2 mg/L. In some embodiments, the non-limiting amount of pantothenate is an amount above 10 mg/L.

In some embodiments, the limiting amount of pantothenate is an amount that is at least 2-fold, 10-fold, 100-fold, 1000-fold, 10,000-fold or 100,000-fold less than a non-limiting amount of pantothenate as determined according to the methods described above. In some embodiments, the limiting amount of pantothenate is an amount that is at least 2-fold, 10-fold, 100-fold, 1000-fold, 10,000-fold or 100,000-fold less than the saturating amount of pantothenate as determined according to the methods described above. In some embodiments, the limiting amount of pantothenate is an amount that is less than 50%, less than 20%, less than 10%, less than 1%, less than 0.5%, less than 0.2%, less than 0.1%, less than 0.01%, or less than 0.001% of a non-limiting amount of pantothenate as determined according to the methods described above. In some embodiments, the limiting amount of pantothenate is an amount that is less than 50%, less than 20%, less than 10%, less than 1%, less than 0.1%, less than 0.01%, or less than 0.001% of the saturating amount of pantothenate as determined according to the methods described above. In other specific embodiments, the limiting amount of pantothenate is an amount less than 10 mg/L, or less than 1 mg/L, or less than 0.2 mg/L, or less than 0.1 mg/L, or less than 0.02 mg/L, or less than 0.01 mg/L, or less than 0.001 mg/L of pantothenate. In a specific embodiment, the limiting amount of pantothenate is 0 mg/L, i.e., no pantothenate. Thus, in this specific embodiment, the host cells are grown during the build stage in a cell culture medium that comprises no external source of pantothenate, and the only source of pantothenate available to the cells is endogenous pantothenate that is internally produced.

In a specific embodiment, the non-limiting amount of pantothenate is the optimal or saturating amount for a given host cell, as described above, and the limiting amount is no pantothenate. In another specific embodiment, the non-limiting amount of pantothenate is at least 0.01 mg/L, and the limiting amount is no pantothenate. In another specific embodiment, the non-limiting amount of pantothenate is an amount of pantothenate from 0.01 to 10 mg/L, and the limiting amount is no pantothenate. In another specific embodiment, the non-limiting amount of pantothenate is at least 10 mg/L, and the limiting amount is no pantothenate.

In some embodiments, the production of the HACD compound during the build stage (step (a) of the method described above) is less than 50, 40, 30, 20 or 10% of the maximum HACD compound production of the genetically modified host cell, i.e., the amount of HACD compound production when the host cell is cultured in medium comprising a saturating or optimal amount of pantothenate. In some embodiments, the production of the HACD compound during the build stage is less than 50% of the maximum HACD compound production of the genetically modified host cell. In some embodiments, the production of the HACD compound during the build stage is less than 40% of the maximum HACD compound production of the genetically modified host cell. In some embodiments, the production of the HACD compound during the build stage is less than 30% of the maximum HACD compound production of the genetically modified host cell. In some embodiments, the production of the HACD compound during the build stage is less than 20% of the maximum HACD compound production of the genetically modified host cell. In some embodiments, the production of the HACD compound during the build stage is less than 10% of the maximum HACD compound production of the genetically modified host cell. In some embodiments, the production of the HACD compound during the build stage is less than 5% of the maximum HACD compound production of the genetically modified host cell. In some embodiments, the production of the HACD compound during the build stage is less than 1% of the maximum HACD compound production of the genetically modified host cell.

In some embodiments, the production of the HACD compound during the production stage (step (b) of the method described above) is greater than 20, 30, 40, 50, 60, 70, 80 or 90% of the maximum HACD compound production of the genetically modified host cell. In some embodiments, the production of the HACD compound during the build stage is greater than 50% of the maximum HACD compound production of the genetically modified host cell. In some embodiments, the production of the HACD compound during the build stage is greater than 60% of the maximum HACD compound production of the genetically modified host cell. In some embodiments, the production of the HACD compound during the build stage is greater than 70% of the maximum HACD compound production of the genetically modified host cell. In some embodiments, the production of the HACD compound during the build stage is greater than 80% of the maximum HACD compound production of the genetically modified host cell. In some embodiments, the production of the HACD compound during the build stage is greater than 90% of the maximum HACD compound production of the genetically modified host cell. In some embodiments, the production of the HACD compound during the build stage is greater than 95% of the maximum HACD compound production of the genetically modified host cell. In some embodiments, the production of the HACD compound during the build stage is 100% or more of the maximum HACD compound production of the genetically modified host cell.

The periods of time for during which the build stage and production stage of the fermentation process are carried out can vary, and will depend on factors such as the growth rates of the host cell, e.g., with pantothenate limitation or supplementation in the culture medium; the intrinsic rate of growth of the host cell; and other culture conditions such as the pH, temperature, and requirements for aerobic, microaerobic, or anaerobic conditions, depending on the specific requirements of the host cell, the fermentation, and the process. However, any duration of the build stage is expected to result in some benefit to the final productivity of the fermentation, since some amount of the negative selective pressure associated with HACD compound production is relieved in the "off" state.

In some embodiments, the build stage is carried out for a period of time sufficient to produce an amount of cellular biomass that can support production of the HACD compound during the production stage. In some embodiments, the build stage is carried out for a period of time sufficient for the population present at the time of inoculation to undergo a plurality of doublings until a desired cell density is reached. In some embodiments, the build stage is carried out for a period of time sufficient for the host cell population to reach a cell density ($OD_{600}$) of between 0.01 and 400 in the fermentation vessel or container in which the build stage is being carried out. In some embodiments, the build stage is carried out until an $OD_{600}$ of at least 0.01 is reached. In some embodiments, the build stage is carried out until an $OD_{600}$ of at least 0.1 is reached. In some embodiments, the build stage is carried out until an $OD_{600}$ of at least 1.0 is reached. In some embodiments, the build stage is carried out until an $OD_{600}$ of at least 10 is reached. In some embodiments, the build stage is carried out until an $OD_{600}$ of at least 100 is reached. In some embodiments, the build stage is carried out until an $OD_{600}$ of between 0.01 and 100 is reached. In some embodiments, the build stage is carried out until an $OD_{600}$ of between 0.1 and 10 is reached. In some embodiments, the build stage is carried out until an $OD_{600}$ of between 1 and 100 is reached. In other embodiments, the build stage is carried for a period of at least 12, 24, 36, 48, 60, 72, 84, 96 or more than 96 hours.

In some embodiments, the production stage is carried out for a period of time sufficient to produce a desired amount of the HACD compound. In some embodiments, the production stage is carried out for a period of at least 12, 24, 36, 48, 60, 72, 84, 96 or more than 96 hours. In some embodiments, the production stage is carried out for a period of between 3 and 20 days. In some embodiments, the production stage is carried for a period of 1, 2, 3, 4, 5, 6, 7, 8, 9, 10, 11, 12, 13, 14, 15, 16, 17, 18, 19, 20 or more than 20 days.

In a particular embodiment, the method of producing an HACD compound comprises conducting fermentation of the genetically modified host cell in a medium comprising a carbon source and a limited or absent pantothenate compound concentration in conditions sufficient to allow growth and maintenance of the genetically modified host cell; then subsequently providing into the culture medium a pantothenate compound at a concentration sufficient to induce production of the HACD compound, and maintaining the concentration of the pantothenate compound throughout the fermentation run.

In another embodiment, the method of producing an HACD compound comprises culturing the host cells in separate build and production culture media. For example, the method can comprise culturing the genetically modified host cell in a build stage wherein the cell is cultured in a medium comprising a limiting amount of pantothenate (e.g., little to no pantothenate) to produce an inoculum, then transferring the inoculum into a second fermentation medium comprising a non-limiting amount of pantothenate, and maintaining steady state conditions in the second fermentation stage to produce a cell culture containing a HACD product.

In some embodiments, the method provided herein is sufficient for producing one or more HACD compounds in an amount greater than about 10 grams per liter of fermentation medium.

In some such embodiments, the HACD derived compound is produced in an amount from about 10 to about 50 grams, more than about 15 grams, more than about 20 grams, more than about 25 grams, or more than about 30 grams per liter of cell culture.

In some embodiments, the method provided herein is sufficient for producing one or more HACD compounds in an amount greater than about 50 milligrams per gram of dry cell weight. In some embodiments, the recombinantly produced HACD compound is produced in an amount from about 50 to about 1500 milligrams, more than about 100 milligrams, more than about 150 milligrams, more than about 200 milligrams, more than about 250 milligrams, more than about 500 milligrams, more than about 750 milligrams, or more than about 1000 milligrams per gram of dry cell weight.

In some embodiments, the practice of the method provided herein results in increased production of the HACD compound by the population of genetically modified host cells, compared to production resulting from a method not comprising a build stage during which the host cells are cultured in a limiting amount of pantothenate. In some embodiments, the practice of the method results in the production of one or more HACD compounds in an amount that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the amount of HACD compound produced by a method not comprising a build stage during which the host cells are cultured in a limiting amount of pantothenate, on a per unit volume of cell culture basis.

In some embodiments, the practice of the method results in the production of one or more HACD compounds in an amount that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the amount of HACD compound produced by a method not comprising a build stage during which the host cells are cultured in a limiting amount of pantothenate, on a per unit dry cell weight basis.

In some embodiments, the practice of the method results in the production of one or more HACD compounds in an amount that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the amount of HACD compound produced by a method not comprising a build stage during which the host cells are cultured in a limiting amount of pantothenate, on a per unit volume of cell culture per unit time basis.

In some embodiments, the practice of the method results in the production of one or more HACD compounds in an amount that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the amount of HACD compound produced by a method not comprising a build stage during which the host cells are cultured in a limiting amount of pantothenate, on a per unit dry cell weight per unit time basis.

6.2.2 Culture Media and Conditions

Materials and methods for the maintenance and growth of microbial cultures are well known to those skilled in the art of microbiology or fermentation science (see, for example, Bailey et al., Biochemical Engineering Fundamentals, second edition, McGraw Hill, New York, 1986). Consideration must be given to appropriate culture medium, pH, temperature, and requirements for aerobic, microaerobic, or anaerobic conditions, depending on the specific requirements of the host cell, the fermentation, and the process.

The methods of producing HACD compounds provided herein may be performed in a suitable culture medium (e.g., with or without pantothenate supplementation) in a suitable container, including but not limited to a cell culture plate, a flask, or a fermentor. Further, the methods can be performed at any scale of fermentation known in the art to support industrial production of microbial products. Any suitable fermentor may be used including a stirred tank fermentor, an airlift fermentor, a bubble fermentor, or any combination thereof. In particular embodiments utilizing *Saccharomyces cerevisiae* as the host cell, strains can be grown in a fermentor as described in detail by Kosaric, et al, in Ullmann's Encyclopedia of Industrial Chemistry, Sixth Edition, Volume 12, pages 398-473, Wiley-VCH Verlag GmbH & Co. KDaA, Weinheim, Germany.

In some embodiments, the culture medium for use in the methods of producing HACD compounds as provided herein includes any culture medium in which a genetically modified microorganism capable of producing an HACD compound can subsist, i.e., support and maintain growth and viability, with little or no pantothenate supplementation. In some embodiments, the culture medium, when supplemented with pantothenate, also promotes the biosynthetic pathway necessary to produce the desired HACD compound.

In some embodiments, the culture medium is an aqueous medium comprising assimilable carbon, nitrogen and phosphate sources. Such a medium can also include appropriate salts, minerals, metals and other nutrients. In some embodiments, the carbon source and each of the essential cell nutrients, other than pantothenate compounds, are added incrementally or continuously to the fermentation media, and each required nutrient is maintained at essentially the minimum level needed for efficient assimilation by growing cells, for example, in accordance with a predetermined cell growth curve based on the metabolic or respiratory function of the cells which convert the carbon source to a biomass.

Suitable conditions and suitable media for culturing microorganisms are well known in the art. In some embodiments, the suitable medium is supplemented with one or more additional agents, such as, for example, an inducer (e.g., when one or more nucleotide sequences encoding a gene product are under the control of an inducible promoter), a repressor (e.g., when one or more nucleotide sequences encoding a gene product are under the control of a repressible promoter), or a selection agent (e.g., an antibiotic to select for microorganisms comprising the genetic modifications).

In some embodiments, the carbon source is a monosaccharide (simple sugar), a disaccharide, a polysaccharide, a non-fermentable carbon source, or one or more combinations thereof. Non-limiting examples of suitable monosaccharides include glucose, galactose, mannose, fructose, ribose, and combinations thereof. Non-limiting examples of suitable disaccharides include sucrose, lactose, maltose, trehalose, cellobiose, and combinations thereof. Non-limiting examples of suitable polysaccharides include starch, glycogen, cellulose, chitin, and combinations thereof. Non-limiting examples of suitable non-fermentable carbon sources include acetate and glycerol.

The concentration of a carbon source, such as glucose, in the culture medium should promote cell growth, but not be so high as to repress growth of the microorganism used. Typically, cultures are run with a carbon source, such as glucose, being added at levels to achieve the desired level of growth and biomass, but at undetectable levels (with detection limits being about <0.1 g/l). In other embodiments, the concentration of a carbon source, such as glucose, in the culture medium is greater than about 1 g/L, preferably greater than about 2 g/L, and more preferably greater than about 5 g/L. In addition, the concentration of a carbon source, such as glucose, in the culture medium is typically less than about 100 g/L, preferably less than about 50 g/L, and more preferably less than about 20 g/L. It should be noted that references to culture component concentrations can refer to both initial and/or ongoing component concentrations. In some cases, it may be desirable to allow the culture medium to become depleted of a carbon source during culture.

Sources of assimilable nitrogen that can be used in a suitable culture medium include, but are not limited to, simple nitrogen sources, organic nitrogen sources and complex nitrogen sources. Such nitrogen sources include anhydrous ammonia, ammonium salts and substances of animal, vegetable and/or microbial origin. Suitable nitrogen sources include, but are not limited to, protein hydrolysates, microbial biomass hydrolysates, peptone, yeast extract, ammonium sulfate, urea, and amino acids. Typically, the concentration of the nitrogen sources, in the culture medium is greater than about 0.1 g/L, preferably greater than about 0.25 g/L, and more preferably greater than about 1.0 g/L. Beyond certain concentrations, however, the addition of a nitrogen source to the culture medium is not advantageous for the growth of the microorganisms. As a result, the concentration of the nitrogen sources, in the culture medium is less than about 20 g/L, preferably less than about 10 g/L and more preferably less than about 5 g/L. Further, in some instances it may be desirable to allow the culture medium to become depleted of the nitrogen sources during culture.

The effective culture medium can contain other compounds such as inorganic salts, vitamins, trace metals or growth promoters. Such other compounds can also be present in carbon, nitrogen or mineral sources in the effective medium or can be added specifically to the medium. The culture medium can also contain a suitable phosphate source. Such phosphate sources include both inorganic and organic phosphate sources. Preferred phosphate sources include, but are not limited to, phosphate salts such as mono or dibasic sodium and potassium phosphates, ammonium phosphate and mixtures thereof. Typically, the concentration of phosphate in the culture medium is greater than about 1.0 g/L, preferably greater than about 2.0 g/L and more preferably greater than about 5.0 g/L. Beyond certain concentrations, however, the addition of phosphate to the culture medium is not advantageous for the growth of the microorganisms. Accordingly, the concentration of phosphate in the culture medium is typically less than about 20 g/L, preferably less than about 15 g/L and more preferably less than about 10 g/L.

A suitable culture medium can also include a source of magnesium, preferably in the form of a physiologically acceptable salt, such as magnesium sulfate heptahydrate, although other magnesium sources in concentrations that contribute similar amounts of magnesium can be used. Typically, the concentration of magnesium in the culture medium is greater than about 0.5 g/L, preferably greater than about 1.0 g/L, and more preferably greater than about 2.0 g/L. Beyond certain concentrations, however, the addition of magnesium to the culture medium is not advantageous for the growth of the microorganisms. Accordingly, the concentration of magnesium in the culture medium is typically less than about 10 g/L, preferably less than about 5 g/L, and more preferably less than about 3 g/L. Further, in some instances it may be desirable to allow the culture medium to become depleted of a magnesium source during culture.

In some embodiments, the culture medium can also include a biologically acceptable chelating agent, such as the dihydrate of trisodium citrate. In such instance, the concentration of a chelating agent in the culture medium is greater than about 0.2 g/L, preferably greater than about 0.5 g/L, and more preferably greater than about 1 g/L. Beyond certain concentrations, however, the addition of a chelating agent to the culture medium is not advantageous for the growth of the microorganisms. Accordingly, the concentration of a chelating agent in the culture medium is typically less than about 10 g/L, preferably less than about 5 g/L, and more preferably less than about 2 g/L.

The culture medium can also initially include a biologically acceptable acid or base to maintain the desired pH of the culture medium. Biologically acceptable acids include, but are not limited to, hydrochloric acid, sulfuric acid, nitric acid, phosphoric acid and mixtures thereof. Biologically acceptable bases include, but are not limited to, ammonium hydroxide, sodium hydroxide, potassium hydroxide and mixtures thereof. In some embodiments, the base used is ammonium hydroxide.

The culture medium can also include a biologically acceptable calcium source, including, but not limited to, calcium chloride. Typically, the concentration of the calcium source, such as calcium chloride, dihydrate, in the culture medium is within the range of from about 5 mg/L to about 2000 mg/L, preferably within the range of from about 20 mg/L to about 1000 mg/L, and more preferably in the range of from about 50 mg/L to about 500 mg/L.

The culture medium can also include sodium chloride. Typically, the concentration of sodium chloride in the culture medium is within the range of from about 0.1 g/L to about 5 g/L, preferably within the range of from about 1 g/L to about 4 g/L, and more preferably in the range of from about 2 g/L to about 4 g/L.

In some embodiments, the culture medium can also include trace metals. Such trace metals can be added to the culture medium as a stock solution that, for convenience, can be prepared separately from the rest of the culture medium. Typically, the amount of such a trace metals solution added to the culture medium is greater than about 1 ml/L, preferably greater than about 5 mL/L, and more preferably greater than about 10 mL/L. Beyond certain concentrations, however, the addition of a trace metals to the culture medium is not advantageous for the growth of the microorganisms. Accordingly, the amount of such a trace metals solution added to the culture medium is typically less than about 100 mL/L, preferably less than about 50 mL/L, and more preferably less than about 30 mL/L. It should be noted that, in addition to adding trace metals in a stock solution, the individual components can be added separately, each within ranges corresponding independently to the amounts of the components dictated by the above ranges of the trace metals solution.

In addition to pantothenate or B5, which may be absent or present from the culture medium depending on the stage of fermentation, the culture media can include other vitamins, such as biotin, calcium, pantothenate, inositol, pyridoxine-HCl, and thiamine-HCl. Such vitamins can be added to the culture medium as a stock solution that, for convenience, can be prepared separately from the rest of the culture medium. Beyond certain concentrations, however, the addition of vitamins to the culture medium is not advantageous for the growth of the microorganisms.

The fermentation methods described herein can be performed in conventional culture modes, which include, but are not limited to, batch, fed-batch, cell recycle, continuous and semi-continuous. In some embodiments, the fermentation is carried out in fed-batch mode. In such a case, some of the components of the medium are depleted during culture, including pantothenate during the production stage of the fermentation. In some embodiments, the culture may be supplemented with relatively high concentrations of such components at the outset, for example, of the production stage, so that growth and/or HACD compound production is supported for a period of time before additions are required. The preferred ranges of these components are maintained throughout the culture by making additions as levels are depleted by culture. Levels of components in the culture medium can be monitored by, for example, sampling the culture medium periodically and assaying for concentrations. Alternatively, once a standard culture procedure is developed, additions can be made at timed intervals corresponding to known levels at particular times throughout the culture. As will be recognized by those in the art, the rate of consumption of nutrient increases during culture as the cell density of the medium increases. Moreover, to avoid introduction of foreign microorganisms into the culture medium, addition is performed using aseptic addition methods, as are known in the art. In addition, a small amount of anti-foaming agent may be added during the culture.

The temperature of the culture medium can be any temperature suitable for growth of the genetically modified cells and/or production of HACD compounds. For example, prior to inoculation of the culture medium with an inoculum, the culture medium can be brought to and maintained at a temperature in the range of from about 20° C. to about 45° C., preferably to a temperature in the range of from about 25° C. to about 40° C., and more preferably in the range of from about 28° C. to about 32° C.

The pH of the culture medium can be controlled by the addition of acid or base to the culture medium. In such cases when ammonia is used to control pH, it also conveniently serves as a nitrogen source in the culture medium. Preferably, the pH is maintained from about 3.0 to about 8.0, more preferably from about 3.5 to about 7.0, and most preferably from about 4.0 to about 6.5.

The culture medium can also be maintained to have a dissolved oxygen content during the course of culture to maintain cell growth and to maintain cell metabolism for production of HACD compounds. The oxygen concentration of the culture medium can be monitored using known methods, such as through the use of an oxygen electrode. Oxygen can be added to the culture medium using methods known in the art, through agitation and aeration of the medium by stirring, shaking or sparging. Preferably, the oxygen concentration in the culture medium is in the range of from about 20% to about 100% of the saturation value of oxygen in the medium based upon the solubility of oxygen in the culture medium at atmospheric pressure and at a temperature in the range of from about 20° C. to about 40° C. Periodic drops in the oxygen concentration below this range may occur during culture, however, without adversely affecting the culture.

Although aeration of the medium has been described herein in relation to the use of air, other sources of oxygen can be used. Particularly useful is the use of an aerating gas that contains a volume fraction of oxygen greater than the volume fraction of oxygen in ambient air. In addition, such aerating gases can include other gases, which do not negatively affect the culture.

In some embodiments, the carbon source concentration, such as the glucose concentration, of the culture medium is monitored during culture. Glucose concentration of the culture medium can be monitored using known techniques, such as, for example, use of the glucose oxidase enzyme test or high pressure liquid chromatography, which can be used to monitor glucose concentration in the supernatant, e.g., a cell-free component of the culture medium. As stated previously, the carbon source concentration should be kept below the level at which cell growth inhibition occurs. Although such concentration may vary from organism to organism, for glucose as a carbon source, cell growth inhibition occurs at glucose concentrations greater than at about 60 g/L, and can be determined readily by trial. Accordingly, when glucose is used as a carbon source the glucose is preferably fed to the fermentor and maintained below detection limits. Alternatively, the glucose concentration in the culture medium is maintained in the range of from about 1 g/L to about 100 g/L, more preferably in the range of from about 2 g/L to about 50 g/L, and yet more preferably in the range of from about 5 g/L to about 20 g/L. Although the carbon source concentration can be maintained within desired levels by addition of, for example, a substantially pure glucose solution, it is acceptable, and may be preferred, to maintain the carbon source concentration of the culture medium by addition of aliquots of the original culture medium. The use of aliquots of the original culture medium may be desirable because the concentrations of other nutrients in the medium (e.g. the nitrogen and phosphate sources) can be maintained simultaneously. Likewise, the trace metals concentrations can be maintained in the culture medium by addition of aliquots of the trace metals solution.

6.2.3 Recovery of HACD Compounds

Once the HACD is produced by the host cell, it may be recovered or isolated for subsequent use using any suitable separation and purification methods known in the art. In some embodiments, an organic phase comprising the HACD is separated from the fermentation by centrifugation. In other embodiments, an organic phase comprising the HACD compound separates from the fermentation spontaneously. In other embodiments, an organic phase comprising the HACD derived compound is separated from the fermentation by adding a deemulsifier and/or a nucleating agent into the fermentation reaction. Illustrative examples of deemulsifiers include flocculants and coagulants. Illustrative examples of nucleating agents include droplets of the HACD compound itself and organic solvents such as dodecane, isopropyl myristate, and methyl oleate.

The HACD compound produced in these cells may be present in the culture supernatant and/or associated with the host cells. In embodiments where the HACD compound is associated with the host cell, the recovery of the HACD may comprise a method of permeabilizing or lysing the cells.

Alternatively or simultaneously, the HACD in the culture medium can be recovered using a recovery process including, but not limited to, chromatography, extraction, solvent extraction, membrane separation, electrodialysis, reverse osmosis, distillation, chemical derivatization and crystallization.

In some embodiments, the HACD compound is separated from other products that may be present in the organic phase. In some embodiments, separation is achieved using adsorption, distillation, gas-liquid extraction (stripping), liquid-liquid extraction (solvent extraction), ultrafiltration, and standard chromatographic techniques.

In some embodiments, the recovered HACD compound is pure, e.g., at least about 40% pure, at least about 50% pure, at least about 60% pure, at least about 70% pure, at least about 80% pure, at least about 90% pure, at least about 95% pure, at least about 98% pure, or more than 98% pure, where "pure" in the context of an HACD compound refers to an HACD compound that is free from other HACD compounds, contaminants, etc.

6.3 Genetically Modified Microorganisms

Provided herein are genetically modified microorganisms (e.g., a genetically modified *Saccharomyces cerevisiae* cell) that produce heterologous acetyl-CoA derived (HACD) compound. The genetically modified microorganisms produce greater amounts of one or more compounds biosynthesized from acetyl-CoA compared to a parent microorganism lacking the genetic modifications described herein.

Methods for genetically modifying microbes using expression vectors or chromosomal integration constructs, e.g., to effect increased production of one or more HACD compounds in a host cell, are well known in the art. See, for example, Sherman, F., et al., *Methods Yeast Genetics*, Cold Spring Harbor Laboratory, N.Y. (1978); Guthrie, C., et al. (Eds.) *Guide To Yeast Genetics and Molecular Biology* Vol. 194, Academic Press, San Diego (1991); Sambrook et al., 2001, *Molecular Cloning—A Laboratory Manual*, $3^{rd}$ edition, Cold Spring Harbor Laboratory, Cold Spring Harbor, N.Y.; and Ausubel et al., eds., Current Edition, *Current Protocols in Molecular Biology*, Greene Publishing Associates and Wiley Interscience, NY.; the disclosures of which are incorporated herein by reference. In addition, inhibition of gene expression, e.g., which results in increased production of one or more HACD compounds in the cell, may be accomplished by deletion, mutation, and/or gene rearrangement. It can also be carried out with the use of antisense RNA, siRNA, miRNA, ribozymes, triple stranded DNA, and transcription and/or translation inhibitors. In addition, transposons can be employed to disrupt gene expression, for example, by inserting it between the promoter and the coding region, or between two adjacent genes to inactivate one or both genes.

In some embodiments, increased production of HACD compound in the cell is effected by the use of expression vectors to express a particular protein, e.g., a protein involved in a biosynthetic pathway as described above. Generally, expression vectors are recombinant polynucleotide molecules comprising replication signals and expression control sequences, e.g., promoters and terminators, operatively linked to a nucleotide sequence encoding a polypeptide. Expression vectors useful for expressing polypeptide-encoding nucleotide sequences include viral vectors (e.g., retroviruses, adenoviruses and adeno-associated viruses), plasmid vectors, and cosmids. Illustrative examples of expression vectors suitable for use in yeast cells include, but are not limited to CEN/ARS and 2μ plasmids. Illustrative examples of promoters suitable for use in yeast cells include, but are not limited to the promoter of the TEF1 gene of *K. lactis*, the promoter of the PGK1 gene of *Saccharomyces cerevisiae*, the promoter of the TDH3 gene of *Saccharomyces cerevisiae*, repressible promoters, e.g., the promoter of the CTR3 gene of *Saccharomyces cerevisiae*, and inducible promoters, e.g., galactose inducible promoters of *Saccharomyces cerevisiae* (e.g., promoters of the GAL1, GAL7, and GAL10 genes). Expression vectors and chromosomal integration constructs can be introduced into microbial cells by any method known to one of skill in the art without limitation. See, for example, Hinnen et al., *Proc. Natl. Acad. Sci. USA* 75:1292-3 (1978); Cregg et al., *Mol. Cell. Biol.* 5:3376-3385 (1985); U.S. Pat. No. 5,272,065; Goeddel et al., eds, 1990, Methods in Enzymology, vol. 185, Academic Press, Inc., CA; Krieger, 1990, *Gene Transfer and Expression—A Laboratory Manual*, Stockton Press, NY; Sambrook et al., 1989, *Molecular Cloning—A Laboratory Manual*, Cold Spring Harbor Laboratory, NY; and Ausubel et al., eds., Current Edition, *Current Protocols in Molecular Biology*, Greene Publishing Associates and Wiley Interscience, NY. Exemplary techniques include, but are not limited to, spheroplasting, electroporation, PEG 1000 mediated transformation, and lithium acetate or lithium chloride mediated transformation.

6.3.1 Host Cells

Cells useful in the methods and compositions provided herein include any cell capable of naturally or recombinantly producing an HACD compound, e.g., an isoprenoid, a polyketide, a fatty acid, and the like. In some embodiments, the cell is a prokaryotic cell. In some embodiments, the cell is a bacterial cell. In some embodiments, the cell is an *Escherichia coli* cell. In some embodiments, the cell is a eukaryotic cell. In some embodiments, the cell is a mammalian cell. In some embodiments, the cell is a Chinese hamster ovary (CHO) cell, a COS-7 cell, a mouse fibroblast cell, a mouse embryonal carcinoma cell, or a mouse embryonic stem cell. In some embodiments, the cell is an insect cell. In some embodiments, the cell is a S2 cell, a Schneider cell, a S12 cell, a 5B1-4 cell, a Tn5 cell, or a Sf9 cell. In some embodiments, the cell is a unicellular eukaryotic organism cell.

In some embodiments, the cell is a mycelial bacterial cell. In some embodiments, the mycelial bacterial cell is of the class actinomycetes. In particular embodiments, the mycelial bacterial cell is of the genera *Streptomyces*, for example, *Streptomyces ambofaciens, Streptomyces avermitilis, Streptomyces azureus, Streptomyces cinnamonensis, Streptomyces coelicolor, Streptomyces curacoi, Streptomyces erythraeus, Streptomyces fradiae, Streptomyces galilaeus, Streptomyces glaucescens, Streptomyces hygroscopicus, Streptomyces lividans, Streptomyces parvulus, Streptomyces peucetius, Streptomyces rimosus, Streptomyces roseofulvus, Streptomyces thermotolerans, Streptomyces violaceoruber.*

In another embodiment, the cell is a fungal cell. In a more particular embodiment, the cell is a yeast cell. Yeasts useful in the methods and compositions provided herein include yeasts that have been deposited with microorganism depositories (e.g. IFO, ATCC, etc.) and belong to the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces,*

*Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis,* and *Zygozyma,* among others.

In particular embodiments, useful yeasts in the methods and compositions provided herein include *Saccharomyces cerevisiae, Pichia pastoris, Schizosaccharomyces pombe, Dekkera bruxellensis, Kluyveromyces lactis* (previously called *Saccharomyces lactis*), *Kluveromyces marxianus, Arxula adeninivorans,* or *Hansenula* polymorphs (now known as *Pichia angusta*). In some embodiments, the microbe is a strain of the genus *Candida,* such as *Candida lipolytica, Candida guilliermondii, Candida krusei, Candida pseudotropicalis,* or *Candida utilis.* In a particular embodiment, the cell is a *Saccharomyces cerevisiae* cell. In some embodiments, the strain of the *Saccharomyces cerevisiae* cell is selected from the group consisting of Baker's yeast, CBS 7959, CBS 7960, CBS 7961, CBS 7962, CBS 7963, CBS 7964, IZ-1904, TA, BG-1, CR-1, SA-1, M-26, Y-904, PE-2, PE-5, VR-1, BR-1, BR-2, ME-2, VR-2, MA-3, MA-4, CAT-1, CB-1, NR-1, BT-1, and AL-1. In some embodiments, the strain of *Saccharomyces cerevisiae* is selected from the group consisting of PE-2, CAT-1, VR-1, BG-1, CR-1, and SA-1. In a particular embodiment, the strain of *Saccharomyces cerevisiae* is PE-2. In another particular embodiment, the strain of *Saccharomyces cerevisiae* is CAT-1. In another particular embodiment, the strain of *Saccharomyces cerevisiae* is BG-1.

In some embodiments, the cell is a haploid microbial cell. In other embodiments, the cell is a diploid microbial cell. In some embodiments, the cell is heterozygous. In other embodiments, the cell is homozygous other than for its mating type allele (i.e., if the cell should sporulate, the resulting four haploid microbial cells would be genetically identical except for their mating type allele, which in two of the haploid cells would be mating type a and in the other two haploid cells would be mating type alpha).

In some embodiments, the cell is a cell that is suitable for industrial fermentation, e.g., bioethanol fermentation. In particular embodiments, the cell is conditioned to subsist under high solvent concentration, high temperature, expanded substrate utilization, nutrient limitation, osmotic stress due, acidity, sulfite and bacterial contamination, or combinations thereof, which are recognized stress conditions of the industrial fermentation environment.

Exemplary HACD compound producing cells, e.g., cells recombinantly producing isoprenoids, polyketides, and fatty acids, and methods for generating such cells, are provided below.

6.4 Production of Isoprenoids

In some embodiments, the HACD compound is an isoprenoid. Isoprenoids are derived from IPP, which in yeast is biosynthesized by enzymes of the MEV pathway (FIG. 6). IPP generated via the MEV pathway can be converted to its isomer, DMAPP, condensed, and modified through the action of various additional enzymes to form simple and more complex HACD isoprenoid compounds (FIG. 7).

In some embodiments, the genetically modified microorganism disclosed herein comprises a heterologous nucleotide sequence encoding an enzyme selected from the group consisting of MEV pathway enzymes, IPP isomerases, polyprenyl synthases, and enzymes that can modify a polyprenyl to form a hemiterpene, a monoterpene, a sesquiterpene, a diterpene, a triterpene, a tetraterpene, a polyterpene, a steroid compound, a carotenoid, or a modified HACD compound.

In some embodiments, the isoprenoid producing cell comprises a heterologous nucleotide sequence encoding an enzyme that can condense two molecules of acetyl-coenzyme A to form acetoacetyl-CoA, e.g., an acetyl-CoA thiolase. Illustrative examples of nucleotide sequences encoding such an enzyme include, but are not limited to: (NC_000913 REGION: 2324131.2325315; *Escherichia coli*), (D49362; *Paracoccus denitrificans*), and (L20428; *Saccharomyces cerevisiae*).

In some embodiments, the isoprenoid producing cell comprises a heterologous nucleotide sequence encoding an enzyme that can condense acetoacetyl-CoA with another molecule of acetyl-CoA to form 3-hydroxy-3-methylglutaryl-CoA (HMG-CoA), e.g., a HMG-CoA synthase. Illustrative examples of nucleotide sequences encoding such an enzyme include, but are not limited to: (NC_001145. complement 19061.20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC_002758, Locus tag SAV2546, GeneID 1122571; *Staphylococcus aureus*).

In some embodiments, the isoprenoid producing cell comprises a heterologous nucleotide sequence encoding an enzyme that can convert HMG-CoA into mevalonate, e.g., a HMG-CoA reductase. Illustrative examples of nucleotide sequences encoding such an enzyme include, but are not limited to: (NM_206548; *Drosophila melanogaster*), (NC_002758, Locus tag SAV2545, GeneID 1122570; *Staphylococcus aureus*), (NM_204485; *Gallus gallus*), (AB015627; *Streptomyces* sp. KO 3988), (AF542543; *Nicotiana attenuata*), (AB037907; *Kitasatospora griseola*), (AX128213, providing the sequence encoding a truncated HMGR; *Saccharomyces cerevisiae*), and (NC_001145: complement (115734.118898; *Saccharomyces cerevisiae*).

In some embodiments, the isoprenoid producing cell comprises a heterologous nucleotide sequence encoding an enzyme that can convert mevalonate into mevalonate 5-phosphate, e.g., a mevalonate kinase. Illustrative examples of nucleotide sequences encoding such an enzyme include, but are not limited to: (L77688; *Arabidopsis thaliana*), and (X55875; *Saccharomyces cerevisiae*).

In some embodiments, the isoprenoid producing cell comprises a heterologous nucleotide sequence encoding an enzyme that can convert mevalonate 5-phosphate into mevalonate 5-pyrophosphate, e.g., a phosphomevalonate kinase. Illustrative examples of nucleotide sequences encoding such an enzyme include, but are not limited to: (AF429385; *Hevea brasiliensis*), (NM_006556; *Homo sapiens*), and (NC_001145. complement 712315.713670; *Saccharomyces cerevisiae*).

In some embodiments, the isoprenoid producing cell comprises a heterologous nucleotide sequence encoding an enzyme that can convert mevalonate 5-pyrophosphate into IPP, e.g., a mevalonate pyrophosphate decarboxylase. Illustrative examples of nucleotide sequences encoding such an enzyme include, but are not limited to: (X97557; *Saccharomyces cerevisiae*), (AF290095; *Enterococcus faecium*), and (U49260; *Homo sapiens*).

In some embodiments, the isoprenoid producing cell comprises a heterologous nucleotide sequence encoding an enzyme that can convert IPP generated via the MEV pathway into DMAPP, e.g., an IPP isomerase. Illustrative examples of nucleotide sequences encoding such an enzyme include but are not limited to: (NC_000913, 3031087.3031635; *Escherichia coli*), and (AF082326; *Haematococcus pluvialis*).

In some embodiments, the isoprenoid producing cell further comprises a heterologous nucleotide sequence encoding a polyprenyl synthase that can condense IPP and/or DMAPP molecules to form polyprenyl compounds containing more than five carbons.

In some embodiments, the isoprenoid producing cell comprises a heterologous nucleotide sequence encoding an enzyme that can condense one molecule of IPP with one molecule of DMAPP to form one molecule of geranyl pyrophosphate ("GPP"), e.g., a GPP synthase. Illustrative examples of nucleotide sequences encoding such an enzyme include, but are not limited to: (AF513111; *Abies grandis*), (AF513112; *Abies grandis*), (AF513113; *Abies grandis*), (AY534686; *Antirrhinum majus*), (AY534687; *Antirrhinum majus*), (Y17376; *Arabidopsis thaliana*), (AE016877, Locus AP11092; *Bacillus cereus*; ATCC 14579), (AJ243739; *Citrus sinensis*), (AY534745; *Clarkia breweri*), (AY953508; *Ips pini*), (DQ286930; *Lycopersicon esculentum*), (AF182828; *Mentha x piperita*), (AF182827; *Mentha x piperita*), (MPI249453; *Mentha x piperita*), (PZE431697, Locus CAD24425; *Paracoccus zeaxanthinifaciens*), (AY866498; *Picrorhiza kurrooa*), (AY351862; *Vitis vinifera*), and (AF203881, Locus AAF12843; *Zymomonas mobilis*).

In some embodiments, the isoprenoid producing cell comprises a heterologous nucleotide sequence encoding an enzyme that can condense two molecules of IPP with one molecule of DMAPP, or add a molecule of IPP to a molecule of GPP, to form a molecule of farnesyl pyrophosphate ("FPP"), e.g., a FPP synthase. Illustrative examples of nucleotide sequences that encode such an enzyme include, but are not limited to: (ATU80605; *Arabidopsis thaliana*), (ATHFPS2R; *Arabidopsis thaliana*), (AAU36376; *Artemisia annua*), (AF461050; *Bos taurus*), (D00694; *Escherichia coli* K-12), (AE009951, Locus AAL95523; *Fusobacterium nucleatum* subsp. *nucleatum* ATCC 25586), (GFFPPSGEN; *Gibberella fujikuroi*), (CP000009, Locus AAW60034; *Gluconobacter oxydans* 621H), (AF019892; *Helianthus annuus*), (HUMFAPS; *Homo sapiens*), (KLPFPSQCR; *Kluyveromyces lactis*), (LAU15777; *Lupinus albus*), (LAU20771; *Lupinus albus*), (AF309508; *Mus musculus*), (NCFPPSGEN; *Neurospora crassa*), (PAFPS1; *Parthenium argentatum*), (PAFPS2; *Parthenium argentatum*), (RATFAPS; *Rattus norvegicus*), (YSCFPP; *Saccharomyces cerevisiae*), (D89104; *Schizosaccharomyces pombe*), (CP000003, Locus AAT87386; *Streptococcus pyogenes*), (CP000017, Locus AAZ51849; *Streptococcus pyogenes*), (NC_008022, Locus YP_598856; *Streptococcus pyogenes* MGAS10270), (NC_008023, Locus YP_600845; *Streptococcus pyogenes* MGAS2096), (NC_008024, Locus YP_602832; *Streptococcus pyogenes* MGAS10750), (MZEFPS; *Zea mays*), (AE000657, Locus AAC06913; *Aquifex aeolicus* VF5), (NM_202836; *Arabidopsis thaliana*), (D84432, Locus BAA12575; *Bacillus subtilis*), (U12678, Locus AAC28894; *Bradyrhizobium japonicum* USDA 110), (BACFDPS; *Geobacillus stearothermophilus*), (NC_002940, Locus NP_873754; *Haemophilus ducreyi* 35000HP), (L42023, Locus AAC23087; *Haemophilus influenzae* Rd KW20), (J05262; *Homo sapiens*), (YP_395294; *Lactobacillus sakei* subsp. *sakei* 23K), (NC_005823, Locus YP_000273; *Leptospira interrogans* serovar Copenhageni str. Fiocruz L1-130), (AB003187; *Micrococcus luteus*), (NC_002946, Locus YP_208768; *Neisseria gonorrhoeae* FA 1090), (U00090, Locus AAB91752; *Rhizobium* sp. NGR234), (J05091; *Saccharomyces cerevisae*), (CP000031, Locus AAV93568; *Silicibacter pomeroyi* DSS-3), (AE008481, Locus AAK99890; *Streptococcus pneumoniae* R6), and (NC_004556, Locus NP_779706; *Xylella fastidiosa* Temecula1).

In some embodiments, the isoprenoid producing cell further comprises a heterologous nucleotide sequence encoding an enzyme that can combine IPP and DMAPP or IPP and FPP to form geranylgeranyl pyrophosphate ("GGPP"). Illustrative examples of nucleotide sequences that encode such an enzyme include, but are not limited to: (ATHGERPYRS; *Arabidopsis thaliana*), (BT005328; *Arabidopsis thaliana*), (NM_119845; *Arabidopsis thaliana*), (NZ_AAJM01000380, Locus ZP_00743052; *Bacillus thuringiensis* serovar *israelensis*, ATCC 35646 sq1563), (CRGGPPS; *Catharanthus roseus*), (NZ_AABF02000074, Locus ZP_00144509; *Fusobacterium nucleatum* subsp. *vincentii*, ATCC 49256), (GFGGPPSGN; *Gibberella fujikuroi*), (AY371321; *Ginkgo biloba*), (AB055496; *Hevea brasiliensis*), (AB017971; *Homo sapiens*), (MCI276129; *Mucor circinelloides* f. *lusitanicus*), (AB016044; *Mus musculus*), (AABX01000298, Locus NCU01427; *Neurospora crassa*), (NCU20940; *Neurospora crassa*), (NZ_AAKL01000008, Locus ZP_00943566; *Ralstonia solanacearum* UW551), (AB118238; *Rattus norvegicus*), (SCU31632; *Saccharomyces cerevisiae*), (AB016095; *Synechococcus elongates*), (SAGGPS; *Sinapis alba*), (SSOGDS; *Sulfolobus acidocaldarius*), (NC_007759, Locus YP_461832; *Syntrophus acidotrophicus* SB), (NC_006840, Locus YP_204095; *Vibrio fischeri* ES114), (NM_112315; *Arabidopsis thaliana*), (ERWCRTE; *Pantoea agglomerans*), (D90087, Locus BAA14124; *Pantoea ananatis*), (X52291, Locus CAA36538; *Rhodobacter capsulatus*), (AF195122, Locus AAF24294; *Rhodobacter sphaeroides*), and (NC_004350, Locus NP_721015; *Streptococcus mutans* UA159).

In some embodiments, the genetically modified microorganism disclosed herein further comprises a heterologous nucleotide sequence encoding an enzyme that can modify a polyprenyl to form a hemiterpene, a monoterpene, a sesquiterpene, a diterpene, a triterpene, a tetraterpene, a polyterpene, a steroid compound, a carotenoid, or a modified HACD compound. In some embodiments, the heterologous nucleotide encodes a carene synthase. Illustrative examples of suitable nucleotide sequences include but are not limited to: (AF461460, REGION 43.1926; *Picea abies*) and (AF527416, REGION: 78.1871; *Salvia stenophylla*). In some embodiments, the heterologous nucleotide encodes a geraniol synthase. Illustrative examples of suitable nucleotide sequences include but are not limited to: (AJ457070; *Cinnamomum tenuipilum*), (AY362553; *Ocimum basilicum*), (DQ234300; *Perilla frutescens* strain 1864), (DQ234299; *Perilla citriodora* strain 1861), (DQ234298; *Perilla citriodora* strain 4935), and (DQ088667; *Perilla citriodora*).

In some embodiments, the heterologous nucleotide encodes a linalool synthase. Illustrative examples of a suitable nucleotide sequence include but are not limited to:

(AF497485; *Arabidopsis thaliana*), (AC002294, Locus AAB71482; *Arabidopsis thaliana*), (AY059757; *Arabidopsis thaliana*), (NM_104793; *Arabidopsis thaliana*), (AF154124; *Artemisia annua*), (AF067603; *Clarkia breweri*), (AF067602; *Clarkia concinna*), (AF067601; *Clarkia breweri*), (U58314; *Clarkia breweri*), (AY840091; *Lycopersicon esculentum*), (DQ263741; *Lavandula angustifolia*), (AY083653; *Mentha citrate*), (AY693647; *Ocimum basilicum*), (XM_463918; *Oryza sativa*), (AP004078, Locus BAD07605; *Oryza sativa*), (XM_463918, Locus XP_463918; *Oryza sativa*), (AY917193; *Perilla citriodora*), (AF271259; *Perilla frutescens*), (AY473623; *Picea abies*), (DQ195274; *Picea sitchensis*), and (AF444798; *Perilla frutescens* var. *crispa* cultivar No. 79).

In some embodiments, the heterologous nucleotide encodes a limonene synthase. Illustrative examples of suitable nucleotide sequences include, but are not limited to: (+)-limonene synthases (AF514287, REGION: 47.1867; *Citrus limon*) and (AY055214, REGION: 48.1889; *Agastache rugosa*) and (−)-limonene synthases (DQ195275, REGION: 1.1905; *Picea sitchensis*), (AF006193, REGION: 73.1986; *Abies grandis*), and (MHC4SLSP, REGION: 29.1828; *Mentha spicata*).

In some embodiments, the heterologous nucleotide encodes a myrcene synthase. Illustrative examples of suitable nucleotide sequences include, but are not limited to: (U87908; *Abies grandis*), (AY195609; *Antirrhinum majus*), (AY195608; *Antirrhinum majus*), (NM_127982; *Arabidopsis thaliana* TPS10), (NM_113485; *Arabidopsis thaliana* ATTPS-CIN), (NM_113483; *Arabidopsis thaliana* ATTPS-CIN), (AF271259; *Perilla frutescens*), (AY473626; *Picea abies*), (AF369919; *Picea abies*), and (AJ304839; *Quercus ilex*).

In some embodiments, the heterologous nucleotide encodes an ocimene synthase. Illustrative examples of suitable nucleotide sequences include, but are not limited to: (AY195607; *Antirrhinum majus*), (AY195609; *Antirrhinum majus*), (AY195608; *Antirrhinum majus*), (AK221024; *Arabidopsis thaliana*), (NM_113485; *Arabidopsis thaliana* ATTPS-CIN), (NM_113483; *Arabidopsis thaliana* ATTPS-CIN), (NM_117775; *Arabidopsis thaliana* ATTPS03), (NM_001036574; *Arabidopsis thaliana* ATTPSO$_3$), (NM_127982; *Arabidopsis thaliana* TPS10), (AB110642; *Citrus unshiu* CitMTSL4), and (AY575970; *Lotus corniculatus* var. *japonicus*).

In some embodiments, the heterologous nucleotide encodes an α-pinene synthase. Illustrative examples of suitable nucleotide sequences include, but are not limited to: (+) α-pinene synthase (AF543530, REGION: 1.1887; *Pinus taeda*), (−)α-pinene synthase (AF543527, REGION: 32.1921; *Pinus taeda*), and (+)/(−)α-pinene synthase (AGU87909, REGION: 6111892; *Abies grandis*).

In some embodiments, the heterologous nucleotide encodes a β-pinene synthase. Illustrative examples of suitable nucleotide sequences include, but are not limited to: (−) β-pinene synthases (AF276072, REGION: 1.1749; *Artemisia annua*) and (AF514288, REGION: 26.1834; *Citrus limon*).

In some embodiments, the heterologous nucleotide encodes a sabinene synthase. An illustrative example of a suitable nucleotide sequence includes but is not limited to AF051901, REGION: 26.1798 from *Salvia officinalis*.

In some embodiments, the heterologous nucleotide encodes a γ-terpinene synthase. Illustrative examples of suitable nucleotide sequences include, but are not limited to: (AF514286, REGION: 30.1832 from *Citrus limon*) and (AB110640, REGION 1.1803 from *Citrus unshiu*).

In some embodiments, the heterologous nucleotide encodes a terpinolene synthase. Illustrative examples of a suitable nucleotide sequence include but are not limited to: (AY693650 from *Oscimum basilicum*) and (AY906866, REGION: 10.1887 from *Pseudotsuga menziesii*).

In some embodiments, the heterologous nucleotide encodes an amorphadiene synthase. An illustrative example of a suitable nucleotide sequence is SEQ ID NO. 37 of U.S. Patent Publication No. 2004/0005678.

In some embodiments, the heterologous nucleotide encodes an α-farnesene synthase. Illustrative examples of suitable nucleotide sequences include, but are not limited to DQ309034 from *Pyrus communis* cultivar d'Anjou (pear; gene name AFS1) and AY182241 from *Malus domestica* (apple; gene AFS1). Pechouus et al., *Planta* 219(1):84-94 (2004).

In some embodiments, the heterologous nucleotide encodes a β-farnesene synthase. Illustrative examples of suitable nucleotide sequences include, but are not limited to GenBank accession number AF024615 from *Mentha* x *piperita* (peppermint; gene Tspa11), and AY835398 from *Artemisia annua*. Picaud et al., *Phytochemistry* 66(9): 961-967 (2005).

In some embodiments, the heterologous nucleotide encodes a farnesol synthase. Illustrative examples of suitable nucleotide sequences include, but are not limited to GenBank accession number AF529266 from *Zea mays* and YDR481C from *Saccharomyces cerevisiae* (gene Pho8). Song, L., *Applied Biochemistry and Biotechnology* 128:149-158 (2006).

In some embodiments, the heterologous nucleotide encodes a nerolidol synthase. An illustrative example of a suitable nucleotide sequence includes, but is not limited to AF529266 from *Zea mays* (maize; gene tps1).

In some embodiments, the heterologous nucleotide encodes a patchoulol synthase. Illustrative examples of suitable nucleotide sequences include, but are not limited to AY508730 REGION: 1.1659 from *Pogostemon cablin*.

In some embodiments, the heterologous nucleotide encodes a nootkatone synthase. Illustrative examples of a suitable nucleotide sequence include, but are not limited to AF441124 REGION: 1.1647 from *Citrus sinensis* and AY917195 REGION: 1.1653 from *Perilla frutescens*.

In some embodiments, the heterologous nucleotide encodes an abietadiene synthase. Illustrative examples of suitable nucleotide sequences include, but are not limited to: (U50768; *Abies grandis*) and (AY473621; *Picea abies*).

In some embodiments, the isoprenoid produced by the cell is a $C_5$ isoprenoid. These compounds are derived from one isoprene unit and are also called hemiterpenes. An illustrative example of a hemiterpene is isoprene. In other embodiments, the isoprenoid is a $C_{10}$ isoprenoid. These compounds are derived from two isoprene units and are also called monoterpenes. Illustrative examples of monoterpenes are limonene, citranellol, geraniol, menthol, perillyl alcohol, linalool, thujone, and myrcene. In other embodiments, the isoprenoid is a $C_{15}$ isoprenoid. These compounds are derived from three isoprene units and are also called sesquiterpenes. Illustrative examples of sesquiterpenes are periplanone B, gingkolide B, amorphadiene, artemisinin, artemisinic acid, valencene, nootkatone, epi-cedrol, epi-aristolochene, farnesol, gossypol, sanonin, periplanone, forskolin, and patchoulol (which is also known as patchouli alcohol). In other embodiments, the isoprenoid is a $C_{20}$ isoprenoid. These compounds are derived from four isoprene units and also called diterpenes. Illustrative examples of diterpenes are casbene, eleutherobin, paclitaxel, prostratin, pseudopterosin, and taxadiene. In yet other examples, the isoprenoid is a $C_{20+}$ isoprenoid. These compounds are derived from more than four isoprene units and include: triterpenes ($C_{30}$ isoprenoid compounds derived from 6 isoprene units) such as arbrusideE, bruceantin, testosterone, progesterone, cortisone, digitoxin, and squalene; tetraterpenes ($C_{40}$ isoprenoid compounds derived from 8 isoprenoids) such as β-carotene; and polyterpenes ($C_{40+}$ isoprenoid compounds derived from more than 8 isoprene units) such as polyisoprene. In some embodiments, the isoprenoid is selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene and valencene. Isoprenoid compounds also include, but are not limited to, carotenoids (such as lycopene, α- and β-carotene, α- and β-cryptoxanthin, bixin, zeaxanthin, astaxanthin, and lutein), steroid compounds, and compounds that are composed of isoprenoids modified by other chemical groups, such as mixed terpene-alkaloids, and coenzyme Q-10.

6.5 Production of Polyketides

In some embodiments, the acetyl-derived compound is a polyketide. Polyketides are synthesized by sequential reactions catalyzed by a collection of enzyme activities called polyketide synthases (PKSs), which are large multi-enzyme protein complexes that contain a coordinated group of active sites. Polyketide biosynthesis proceeds stepwise starting from simple 2-, 3-, 4-carbon building blocks such as acetyl-CoA, propionyl CoA, butyryl-CoA and their activated derivatives, malonyl-, methylmalonyl- and ethylmalonyl-CoA, primarily through decarboxylative condensation of malonyl-CoA-derived units via Claisen condensation reactions. The PKS genes are usually organized in one operon in bacteria and in gene clusters in eukaryotes. Three types of polyketide synthases have been characterized: Type I polyketide synthases are large, highly modular proteins subdivided into two classes: 1) iterative PKSs, which reuse domains in a cyclic fashion and 2) modular PKSs, which contain a sequence of separate modules and do not repeat domains. Type II polyketide synthases are aggregates of monofunctional proteins, and Type III polyketide synthases do not use acyl carrier protein domains.

Unlike fatty acid biosynthesis, in which each successive chain elongation step is followed by a fixed sequence of ketoreduction, dehydration and enoyl, reduction as described below, the individual chain elongation intermediates of polyketide biosynthesis undergo all, some, or no functional group modifications, resulting in a large number of chemically diverse products. Additional degrees of complexity arise from the use of different starter units and chain elongation units as well as the generation of new stereoisomers.

The order of complete polyketide-synthesis as directed by a polyketide synthase follows (in the order N-terminus to C-terminus): starting or loading the initial carbon building blocks onto an acyl carrier protein, elongation modules which catalyze the extension of the growing macrolide chain and termination modules that catalyze the release of the synthesized macrolide.

Component domains or separate enzyme functionalities active in this biosynthesis include acyl-transferases for the loading of starter, extender and intermediate acyl units; acyl carrier proteins which hold the growing macrolide as a thiol ester; β-keto-acyl synthases which catalyze chain extension; β-keto reductases responsible for the first reduction to an alcohol functionality; dehydratases which eliminate water to give an unsaturated thiolester; enoyl reductases which catalyze the final reduction to full saturation; and thiolesterases which catalyze macrolide release and cyclization.

In some embodiments, the genetically modified microorganism disclosed herein comprises a heterologous nucleotide sequence encoding an enzyme that can condense at least one of acetyl-CoA and malonyl-CoA with an acyl carrier protein, e.g. an acyl-transferase.

In some embodiments, the genetically modified microorganism disclosed herein comprises a heterologous nucleotide sequence encoding an enzyme that can condense a first reactant selected from the group consisting of acetyl-CoA and malonyl-CoA with a second reactant selected from the group consisting of malonyl-CoA or methylmalonyl-CoA to form a polyketide product, e.g. a β-keto-acyl synthase.

In some embodiments, the genetically modified microorganism disclosed herein comprises a heterologous nucleotide sequence encoding an enzyme that can reduce a β-keto chemical group on a polyketide compound to a β-hydroxy group, e.g. a β-keto reductase.

In some embodiments, the genetically modified microorganism disclosed herein comprises a heterologous nucleotide sequence encoding an enzyme that can dehydrate an alkane chemical group in a polyketide compound to produce an α-β-unsaturated alkene, e.g. a dehydratase.

In some embodiments, the genetically modified microorganism disclosed herein comprises a heterologous nucleotide sequence encoding an enzyme that can reduce an α-β-double-bond in a polyketide compound to a saturated alkane, e.g. an enoyl-reductase.

In some embodiments, the genetically modified microorganism disclosed herein comprises a heterologous nucleotide sequence encoding an enzyme that can hydrolyze a polyketide compound from an acyl carrier protein, e.g. a thioesterase.

In some embodiments, the polyketide producing cell comprises one or more heterologous nucleotide sequences encoding an enzyme comprising a KS catalytic region. In some embodiments, the polyketide producing cell comprises one or more heterologous nucleotide sequences encoding an enzyme comprising an AT catalytic region. In some embodiments, the polyketide producing cell comprises more than one heterologous nucleotide sequence encoding an enzyme comprising an AT catalytic region. In some embodiments, the polyketide producing cell comprises one or more heterologous nucleotide sequences encoding an enzyme comprising a CLF catalytic region. In some embodiments, the polyketide producing cell comprises one or more heterologous nucleotide sequences encoding an enzyme comprising an ACP activity. In some embodiments, the polyketide producing cell comprises more than one heterologous nucleotide sequence encoding an enzyme comprising an ACP activity.

In a particular embodiment, the polyketide producing cell comprises a minimal aromatic PKS system, e.g., heterologous nucleotide sequences encoding an enzyme comprising a KS catalytic region, an enzyme comprising an AT catalytic region, an enzyme comprising a CLF catalytic region, and an enzyme comprising an ACP activity, respectively. In a particular embodiment, the polyketide producing cell comprises a minimal modular PKS system, e.g., heterologous nucleotide sequences encoding an enzyme comprising a KS catalytic region, an enzyme comprising an AT catalytic region, and an enzyme comprising an ACP activity, respectively. In yet another particular embodiment, the polyketide producing cell comprises a modular aromatic PKS system for de novo polyketide synthesis, e.g., heterologous nucleotide sequences encoding an enzyme comprising a KS catalytic region, one or more enzymes comprising an AT catalytic region, and one or more enzymes comprising an ACP activity, respectively.

In some embodiments, the polyketide producing cell comprising a minimal PKS system, e.g., a minimal aromatic PKS system or minimal modular PKS system, further comprises additional catalytic activities which can contribute to production of the end-product polyketide. In some embodiments, the polyketide producing cell comprises one or more heterologous nucleotide sequences encoding an enzyme comprising a cyclase (CYC) catalytic region, which facilitates the cyclization of the nascent polyketide backbone. In some embodiments, the polyketide producing cell comprises one or more heterologous nucleotide sequences encoding an enzyme comprising a ketoreductase (KR) catalytic region. In some embodiments, the polyketide producing cell comprises one or more heterologous nucleotide sequences encoding an enzyme comprising an aromatase (ARO) catalytic region. In some embodiments, the polyketide producing cell comprises one or more heterologous nucleotide sequences encoding an enzyme comprising an enoylreductase (ER) catalytic region. In some embodiments, the polyketide producing cell comprises one or more heterologous nucleotide sequences encoding an enzyme comprising a thioesterase (TE) catalytic region. In some embodiments, the polyketide producing cell further comprises one or more heterologous nucleotide sequences encoding an enzyme comprising a holo ACP synthase activity, which effects pantetheinylation of the ACP.

In some embodiments, the polyketide producing cell further comprises one or more heterologous nucleotide sequences conferring a postsynthesis polyketide modifying activity. In some embodiments, the polyketide producing cell further comprises one or more heterologous nucleotide sequences encoding an enzyme comprising a glycosylase activity, which effects postsynthesis modifications of polyketides, for example, where polyketides having antibiotic activity are desired. In some embodiments, the polyketide producing cell further comprises one or more heterologous nucleotide sequences encoding an enzyme comprising a hydroxylase activity. In some embodiments, the polyketide producing cell further comprises one or more heterologous nucleotide sequences encoding an enzyme comprising an epoxidase activity. In some embodiments, the polyketide producing cell further comprises one or more heterologous nucleotide sequences encoding an enzyme comprising a methylase activity.

In some embodiments, the polyketide producing cell further comprises one or more heterologous nucleotide sequences encoding a biosynthetic enzyme including, but not limited to, at least one polyketide synthesis pathway enzyme, and enzymes that can modify an acetyl-CoA compound to form a polyketide product such as a macrolide, an antibiotic, an antifungal, a cytostatic compound, an anticholesterolemic compound, an antiparasitic compound, a coccidiostatic compound, an animal growth promoter or an insecticide. In some embodiments, the HACD compound is a polyene. In some embodiments, the HACD compound is a cyclic lactone. In some embodiments, the HACD compound comprises a 14, 15, or 16-membered lactone ring. In some embodiments, the HACD compound is a polyketide selected from the group consisting of a polyketide macrolide, antibiotic, antifungal, cytostatic, anticholesterolemic, antiparasitic, a coccidiostatic, animal growth promoter and insecticide.

In some embodiments, the polyketide producing cell comprises heterologous nucleotide sequences, for example sequences encoding PKS enzymes and polyketide modification enzymes, capable of producing a polyketide selected from, but not limited to, the following polyketides: Avermectin (see, e.g., U.S. Pat. No. 5,252,474; U.S. Pat. No. 4,703,009; EP Pub. No. 118,367; MacNeil et al., 1993, "Industrial Microorganisms: Basic and Applied Molecular Genetics"; Baltz, Hegeman, & Skatrud, eds. (ASM), pp. 245-256, "A Comparison of the Genes Encoding the Polyketide Synthases for Avermectin, Erythromycin, and Nemadectin"; MacNeil et al., 1992, Gene 115: 119-125; and Ikeda and Omura, 1997, Chem. Res. 97: 2599-2609); Candicidin (FR008) (see, e.g., Hu et al., 1994, Mol. Microbiol. 14: 163-172); Carbomycin, Curamycin (see, e.g., Bergh et al., Biotechnol Appl Biochem. 1992 February; 15(1):80-9); Daunorubicin (see, e.g., J Bacteria 1994 October; 176(20): 6270-80); Epothilone (see, e.g., PCT Pub. No. 99/66028; and PCT Pub. No. 00/031247); Erythromycin (see, e.g., PCT Pub. No. 93/13663; U.S. Pat. No. 6,004,787; U.S. Pat. No. 5,824,513; Donadio et al., 1991, Science 252:675-9; and Cortes et al., Nov. 8, 1990, Nature 348:176-8); FK-506 (see, e.g., Motamedi et al., 1998; Eur. J Biochem. 256: 528-534; and Motamedi et al., 1997, Eur. J Biochem. 244: 74-80); FK-520 (see, e.g., PCT Pub. No. 00/020601; and Nielsen et al., 1991, Biochem. 30:5789-96); Griseusin (see, e.g., Yu et al., J Bacterial. 1994 May; 176(9):2627-34); Lovastatin (see, e.g., U.S. Pat. No. 5,744,350); Frenolycin (see, e.g., Khosla et al., Bacteriol. 1993 April; 175(8):2197-204; and Bibb et al., Gene 1994 May 3; 142(1):31-9); Granaticin (see, e.g., Sherman et al., EMBO J. 1989 September; 8(9):2717-25; and Bechtold et al., Mol Gen Genet. 1995 Sep. 20; 248(5):610-20); Medermycin (see, e.g., Ichinose et al., Microbiology 2003 July; 149(Pt 7):1633-45); Monensin (see, e.g., Arrowsmith et al., Mol Gen Genet. 1992 August; 234(2):254-64); Nonactin (see, e.g., FEMS Microbiol Lett. 2000 Feb. 1; 183(1):171-5); Nanaomycin (see, e.g., Kitao et al., J Antibiot (Tokyo). 1980 July; 33(7):711-6); Nemadectin (see, e.g., MacNeil et al., 1993, supra); Niddamycin (see, e.g., PCT Pub. No. 98/51695; and Kakavas et al., 1997, J. Bacteriol. 179: 7515-7522); Oleandomycin (see e.g., Swan et al., 1994, Mol. Gen. Genet. 242: 358-362; PCT Pub. No. 00/026349; Olano et al., 1998, Mol. Gen. Genet. 259(3): 299-308; and PCT Pat. App. Pub. No. WO 99/05283); Oxytetracycline (see, e.g., Kim et al., Gene. 1994 Apr. 8; 141(1):141-2); Picromycin (see, e.g., PCT Pub. No. 99/61599; PCT Pub. No. 00/00620; Xue et al., 1998, Chemistry & Biology 5(11): 661-667; Xue et al., October 1998, Proc. Natl. Acad. Sci. USA 95: 12111 12116); Platenolide (see, e.g., EP Pub. No. 791,656; and U.S. Pat. No. 5,945, 320); Rapamycin (see, e.g., Schwecke et al., August 1995, Proc. Natl. Acad. Sci. USA 92:7839-7843; and Aparicio et al., 1996, Gene 169: 9-16); Rifamycin (see, e.g., PCT Pub. No. WO 98/07868; and August et al., Feb. 13, 1998, Chemistry & Biology, 5(2): 69-79); Sorangium (see, e.g., U.S. Pat. No. 6,090,601); Soraphen (see, e.g., U.S. Pat. No. 5,716,849; Schupp et al., 1995, J. Bacteriology 177: 3673-3679); Spinocyn (see, e.g., PCT Pub. No. 99/46387); Spiramycin (see, e.g., U.S. Pat. No. 5,098,837); Tetracenomycin (see, e.g., Summers et al., J Bacteria 1992 March; 174(6):1810-20; and Shen et al., J Bacteria 1992 June; 174(11):3818-21); Tetracycline (see, e.g., J Am Chem Soc. 2009 Dec. 9; 131(48):17677-89); Tylosin (see, e.g., U.S. Pat. No. 5,876,991; U.S. Pat. No. 5,672,497; U.S. Pat. No.

5,149,638; EP Pub. No. 791,655; EP Pub. No. 238,323; Kuhstoss et al., 1996, Gene 183:231-6; and Merson-Davies and Cundliffe, 1994, *Mol. Microbiol.* 13: 349-355); and 6-methylsalicyclic acid (see, e.g., Richardson et al., *Metab Eng.* 1999 April; 1(2):180-7; and Shao et al., *Biochem Biophys Res Commun.* 2006 Jun. 23; 345(1):133-9).

6.6 Production of Fatty Acids

In some embodiments, the HACD compound is a fatty acid. Fatty acids are synthesized by a series of decarboxylative Claisen condensation reactions from acetyl-CoA and malonyl-CoA catalyzed by fatty acid synthases. Similar to polyketide synthases, fatty acid synthases are not a single enzyme but an enzymatic system composed of 272 kDa multifunctional polypeptide in which substrates are handed from one functional domain to the next. Two principal classes of fatty acid synthases have been characterized: Type I fatty acid synthases are single, multifunctional polypeptides common to mammals and fungi (although the structural arrangement of fungal and mammalian synthases differ) and the CMN group of bacteria (*corynebacteria, mycobacteria,* and *nocardia*). Type II synthases, found in archaeabacteria and eubacteria, are a series of discrete, monofunctional enzymes that participate in the synthesis of fatty acids. The mechanisms fatty acid elongation and reduction is the same in the two classes of synthases, as the enzyme domains responsible for these catalytic events are largely homologous amongst the two classes.

Following each round of elongation of the fatty acid chain in the decarboxylative Claisen condensation reactions, the β-keto group is reduced to a fully saturated carbon chain by the sequential action of a ketoreductase, a dehydratase, and an enol reductase. The growing fatty acid chain moves between these active sites attached to an acyl carrier protein and is ultimately released by the action of a thioesterase upon reaching a carbon chain length of 16 (palmitidic acid).

In some embodiments, the genetically modified microorganism disclosed herein comprises a heterologous nucleotide sequence encoding a biosynthetic enzyme including, but not limited to, at least one fatty acid synthesis pathway enzyme, and enzymes that can modify an acetyl-CoA compound to form a fatty acid product such as a palmitate, palmitoyl CoA, palmitoleic acid, sapienic acid, oleic acid, linoleic acid, α-linolenic acid, arachidonic acid, eicosapentaenoic acid, erucic acid, and docosahexaenoic acid. In some embodiments, the HACD compound is a fatty acid selected from the group consisting of palmitate, palmitoyl CoA, palmitoleic acid, sapienic acid, oleic acid, linoleic acid, α-linolenic acid, arachidonic acid, eicosapentaenoic acid, erucic acid, and docosahexaenoic acid.

In some embodiments, the genetically modified microorganism disclosed herein comprises a heterologous nucleotide sequence encoding an enzyme that can covalently link at least one of acetyl-CoA and malonyl-CoA with an acyl carrier protein, e.g. an acyl-transferase. In some embodiments, the genetically modified microorganism disclosed herein comprises a heterologous nucleotide sequence encoding an enzyme that can condense acetyl chemical moiety and a malonyl chemical moiety, each bound to an acyl carrier protein (ACP), to form acetoacetyl-ACP, e.g. a β-Ketoacyl-ACP synthase.

In some embodiments, the genetically modified microorganism disclosed herein comprises a heterologous nucleotide sequence encoding an enzyme that can reduce the double bond in acetoacetyl-ACP with NADPH to form a hydroxyl group in D-3-hydroxybutyryl hydroxylase-ACP, e.g. a β-Ketoacyl-ACP reductase.

In some embodiments, the genetically modified microorganism disclosed herein comprises a heterologous nucleotide sequence encoding an enzyme that can dehydrate D-3-Hydroxybutyryl hydroxylase-ACP to create a double bond between the beta- and gamma-carbons forming crotonyl-ACP, e.g. a β-hydroxyacyl-ACP dehydrase.

In some embodiments, the genetically modified microorganism disclosed herein comprises a heterologous nucleotide sequence encoding an enzyme that can reduce crotonyl ACP with NADPH to form butyryl-ACP, e.g. an enoyl ACP reductase.

In some embodiments, the genetically modified microorganism disclosed herein comprises a heterologous nucleotide sequence encoding an enzyme that can hydrolyze a C16 acyl compound from an acyl carrier protein to form palmitate, e.g. a thioesterase.

In some embodiments, the fatty acid producing cell comprises one or more heterologous nucleotide sequences encoding acetyl-CoA synthase and/or malonyl-CoA synthase, to effect increased production of one or more fatty acids as compared to a genetically unmodified parent cell.

For example, to increase acetyl-CoA production, one or more of the following genes can be expressed in the cell: pdh, panK, aceEF (encoding the E1p dehydrogenase component and the E2p dihydrolipoamide acyltransferase component of the pyruvate and 2-oxoglutarate dehydrogenase complexes), fabH, fabD, fabG, acpP, and fabF. Illustrative examples of nucleotide sequences encoding such enzymes include, but are not limited to: pdh (BAB34380, AAC73227, AAC73226), panK (also known as coaA, AAC76952), aceEF (AAC73227, AAC73226), fabH (AAC74175), fabD (AAC74176), fabG (AAC74177), acpP (AAC74178), fabF (AAC74179).

In some embodiments, increased fatty acid levels can be effected in the cell by attenuating or knocking out genes encoding proteins involved in fatty acid degradation. For example, the expression levels of fadE, gpsA, ldhA, pflb, adhE, pta, poxB, ackA, and/or ackB can be attenuated or knocked-out in an engineered host cell using techniques known in the art. Illustrative examples of nucleotide sequences encoding such proteins include, but are not limited to: fadE (AAC73325), gspA (AAC76632), ldhA (AAC74462), pflb (AAC73989), adhE (AAC74323), pta (AAC75357), poxB (AAC73958), ackA (AAC75356), and ackB (BAB81430). The resulting host cells will have increased acetyl-CoA production levels when grown in an appropriate environment.

In some embodiments, the fatty acid producing cell comprises a heterologous nucleotide sequence encoding an enzyme that can convert acetyl-CoA into malonyl-CoA, e.g., the multisubunit AccABCD protein. An illustrative example of a suitable nucleotide sequence encoding AccABCD includes but is not limited to accession number AAC73296, EC 6.4.1.2.

In some embodiments, the fatty acid producing cell comprises a heterologous nucleotide sequence encoding a lipase. Illustrative examples of suitable nucleotide sequences encoding a lipase include, but are not limited to accession numbers CAA89087 and CAA98876.

In some embodiments, increased fatty acid levels can be effected in the cell by inhibiting PlsB, which can lead to an increase in the levels of long chain acyl-ACP, which will inhibit early steps in the fatty acid biosynthesis pathway (e.g., accABCD, fabH, and fabI). The expression level of PlsB can be attenuated or knocked-out in an engineered host cell using techniques known in the art. An illustrative example of a suitable nucleotide sequence encoding PlsB includes but is not limited to accession number AAC77011. In particular embodiments, the plsB D31 IE mutation can be used to increase the amount of available acyl-CoA in the cell.

In some embodiments, increased production of monounsaturated fatty acids can be effected in the cell by overexpressing an sfa gene, which would result in suppression offabA. An illustrative example of a suitable nucleotide sequence encoding sfa includes but is not limited to accession number AAN79592.

In some embodiments, increased fatty acid levels can be effected in the cell by modulating the expression of an enzyme which controls the chain length of a fatty acid substrate, e.g., a thioesterase. In some embodiments, the fatty acid producing cell has been modified to overexpress a tes or fat gene. Illustrative examples of suitable tes nucleotide sequences include but are not limited to accession numbers: (tesA: AAC73596, from *E. Coli*, capable of producing $C_{18:1}$ fatty acids) and (tesB: AAC73555 from *E. Coli*). Illustrative examples of suitable fat nucleotide sequences include but are not limited to: (fatB: □41635 and AAA34215, from *Umbellularia california*, capable of producing $C_{12:0}$ fatty acids), (fatB2: Q39513 and AAC49269, from *Cuphea hookeriana*, capable of producing $C_{8:0}$-$C_{10:0}$ fatty acids), (fatB3: AAC49269 and AAC72881, from *Cuphea hookeriana*, capable of producing $C_{14:0}$-$C_{16:0}$ fatty acids), (fatB: Q39473 and AAC49151, from *Cinnamonum camphorum*, capable of producing $C_{14:0}$ fatty acids), (fatB [M141T]: CAA85388, from m*Arabidopsis thaliana*, capable of producing $C_{16:1}$ fatty acids), (fatA: NP 189147 and NP 193041, from *Arabidopsis thaliana*, capable of producing $C_{18:1}$ fatty acids), (fatA: CAC39106, from *Bradvrhiizobium japonicum*, capable of preferentially producing $C_{18:1}$ fatty acids), (fatA: AAC72883, from *Cuphea hookeriana*, capable of producing $C_{18:1}$ fatty acids), and (ifatA1, AAL79361 from *Helianthus annus*).

In some embodiments, increased levels of $C_{10}$ fatty acids can be effected in the cell by attenuating the expression or activity of thioesterase $C_{18}$ using techniques known in the art. Illustrative examples of suitable nucleotide sequences encoding thioesterase $C_{18}$ include, but are not limited to accession numbers AAC73596 and P0ADA1. In other embodiments, increased levels of $C_{10}$ fatty acids can be effected in the cell by increasing the expression or activity of thioesterase $C_{10}$ using techniques known in the art. An illustrative example of a suitable nucleotide sequence encoding thioesterase $C_{10}$ includes, but is not limited to accession number Q39513.

In some embodiments, increased levels of $C_{14}$ fatty acids can be effected in the cell by attenuating the expression or activity of endogenous thioesterases that produce non-$C_{14}$ fatty acids, using techniques known in the art. In other embodiments, increased levels of $C_{14}$ fatty acids can be effected in the cell by increasing the expression or activity of thioesterases that use the substrate $C_{14}$-ACP, using techniques known in the art. An illustrative example of a suitable nucleotide sequence encoding such a thioesterase includes, but is not limited to accession number Q39473.

In some embodiments, increased levels of $C_{12}$ fatty acids can be effected in the cell by attenuating the expression or activity of endogenous thioesterases that produce non-$C_{12}$ fatty acids, using techniques known in the art. In other embodiments, increased levels of $C_{12}$ fatty acids can be effected in the cell by increasing the expression or activity of thioesterases that use the substrate $C_{12}$-ACP, using techniques known in the art. An illustrative example of a suitable nucleotide sequence encoding such a thioesterase includes, but is not limited to accession number Q41635.

6.7 Methods of Storing Cells

In some embodiments, the genetically modified host cells capable of producing an HACD compound are more viable and healthy when stored in a medium that is low or absent in pantothenate compounds. In particular, such cells grow better after inoculation into a suitable growth medium and produce more HACD compound during the production stage when stored in a pantothenate compound-free, or low pantothenate-concentration media.

Thus, in another aspect, provided herein is a method of storing a genetically modified host cell capable of producing an HACD compound, the method comprising preparing a composition comprising the genetically modified host cell and a storage medium comprising an assimilable carbon, nitrogen and phosphate source and between 0 μmol/liter and 10 μmol/liter of a pantothenate compound; and freezing the composition. In a specific embodiment, the storage medium contains no detectable pantothenate compound. In another specific embodiment, the storage medium comprises glycerol in an amount ranging between 1 part glycerol:3 parts culture media, up to 3 parts glycerol:1 part culture media. In another specific embodiment, the storage medium is frozen at −80° C.

In another aspect, provided herein is a storage medium containing an assimilable carbon, nitrogen and phosphate source and between 0 μmol/liter and 10 μmol/liter of a pantothenate compound. In a specific embodiment, the storage medium contains no detectable pantothenate compound. In another specific embodiment, the storage medium comprises glycerol in an amount ranging between 1 part glycerol:3 parts culture media, up to 3 parts glycerol:1 part culture media. In another specific embodiment, the storage medium is frozen at −80° C. In another specific embodiment, the storage medium comprises a genetically modified host cell capable of producing an HACD compound.

7. EXAMPLES

7.1 Example 1

This example describes an exemplary method for determining the cell density ($OD_{600}$) of a yeast cell culture.

An 8 μL sample of a cell culture was combined with 92 μL of Triton OD Diluent (20 g/L Triton X-114, 200 mL/L PEG 200, 200 mL/L 100% ethanol, rest water) in a clear 96-well plate, the solution was agitated at 1,000 RPM for 6 minutes, and the $OD_{600}$ was determined by measuring absorbance at 600 nm on an M5 spectrophotometer (Molecular Devices, Sunnyvale, Calif.).

7.2 Example 2

This example describes an exemplary Nile Red based method useful for determining the farnesene titer of yeast cell cultures.

A 98 μL sample of a cell culture was transferred into a 96-well black polystyrene flat bottom assay plate, and 2 μL of Nile Red (Invitrogen, Carlsbad, Calif.) dissolved at 100 μg/mL in DMSO was added to each well. Fluorescence levels were immediately measured on an M5 spectrophotometer with excitation at 500 nm and emission at 550 nm.

7.3 Example 3

This example describes an exemplary gas chromatography (GC) based method useful for determining the farnesene titer of yeast cell cultures.

Sample was extracted with methanol-heptane (1:1 v/v), and the mixture was centrifuged to remove cellular material. An aliquot of the methanol-heptane extract was diluted into n-heptane with 0.001% t-caryohyllene (which served as a retention time marker to monitor successful injection and elution during the specified GC oven profile) and then injected onto a methyl silicone stationary phase using a pulsed split injection. Farnesene was separated by boiling point using GC with flame ionization detection (FID).

7.4 Example 4

This example illustrates the use of a pantothenate compound as a nongenetic switch to enhance biomass build in a first seed culture, followed by enhanced HACD compound production in the production stage of the fermentation process.

a) Preparation of a Seed Culture

A seed medium was prepared containing 2% sucrose BSM (biomass build medium) and 0 mg/L calcium D-pantothenate. The pH of the seed medium was adjusted to pH 7.0 with a NaOH solution. The medium (250 mL) was sterilized and inoculated with one seed vial of genetically modified host cells and incubated at 34° C. for 24-36 hours under aerobic conditions.

b) Main Fermentation Process

A stirred fermentor with a vessel size of 2 liters was filed with a sterile production cell culture medium containing 2% sucrose and 10 mg/L calcium D-pantothenate. Fermentation was carried out at 34° C. for 6 days under aerobic conditions to maximize the production of the HACD product.

7.5 Example 5

This example demonstrates that in cultures of yeast cells genetically engineered to produce higher levels of an exemplary heterologous HACD secondary metabolite, biomass yield can be increased and production of the heterologous secondary metabolite can be reduced by reducing the amount of exogenously provided (R)-pantothenate.

Yeast strains Y4689 and Y4352 each comprise heterologous enzymes, including the following enzymes of the MEV pathway: IPP isomerase, FPP synthase, and farnesene synthase. These strains are capable of producing an exemplary heterologous HACD secondary metabolite (farnesene) at yields of 15% and 13%, respectively.

Cells from yeast strains Y4689 and Y4352 were obtained from exponentially growing cultures, washed three times with water, and then resuspended in 2% sucrose BSM comprising 0 mg/L calcium D-pantothenate. 15 μL taken from each cell suspension was added to biomass build cultures consisting of wells of a 96-well plate containing 360 μL of 2% sucrose BSM comprising either 10 mg/L (100%), 1 mg/L (10%), 0.2 mg/L (2%), 0.1 mg/L (1%), 0.02 mg/L (0.2%), 0.01 mg/L (0.1%), 0.001 mg/L (0.01%), or 0 mg/L of D-pantothenate. The biomass build cultures were incubated for 48 hours in an ATR shaker at 1,000 rpm, 80% humidity, and 34° C., at which time the cultures had reached their maximal $OD_{600}$. The biomass build cultures were then diluted 1:25 into production cultures consisting of wells of a second 96-well plate containing the same media and plate layout as the first 96-well plate. The production cultures were incubated for 48 hours in an ATR shaker at 1,000 rpm, 80% humidity, and 34° C., at which time samples were taken from each well to measure the final biomass (i.e., final cell density) and the farnesene titer, as described in Examples 1 and 2 above, respectively.

FIGS. 3A and 3B show that both strains were severely curtailed in their ability to produce farnesene when pantothenate levels were reduced in the biomass build and production cultures, and that this reduction in the production of exemplary HACD (farnesene) was accompanied by an increase in the final cell biomass. These results demonstrate that pantothenate can be limited or omitted from the culture medium to effectively reduce HACD compound production, and can be added into culture medium to induce or enhance HACD compound production.

7.6 Example 6

This example illustrates that yeast strains that are capable of making commercial quantities of an HACD compound display the unexpected behavior of growing better in the absence of an externally supplied patenothenate compound. In contrast, wildtype yeast and yeast strains making smaller amounts of HACD compounds display the expected behavior of growing better in the presence of externally supplied pantothenate compound than in its absence.

Yeast strains Y4720 and Y5038 each comprise heterologous enzymes, including the following enzymes of the MEV pathway: IPP isomerase, FPP synthase, and farnesene synthase. Strain Y4720 is capable of producing farnesene at yields of 14% while Strain 5038 is capable of making less than half as much farnesene at 6%. Strain Y2205 is a CEN.PK2 wild-type control that does not produce any farnesene.

Exponentially growing cultures of Y4720, Y5038, and Y2205 were diluted in sterile PBS to an $OD_{600}$ of 1, and 20 μL of each dilution was transferred to a well in column 1 of a 96-well plate containing 180 μL of sterile PBS per well. Using a multichannel pipette, 20 μL of column 1 was transferred to column 2, and so on, resulting in 1:10 serial dilutions across the plate. Finally, a sterilized 48-tine pinning tool was used to stamp the cultures from the 96 well-plate onto CSM agar plates comprising either 0.4 mg/L or 0.002 mg/L calcium D-pantothenate. The agar plates were incubated at 30° C. for 112 hours, and colony growth was monitored.

As shown in FIG. 4, colonies of Y4720 were smaller than colonies of the other two strains in the presence of 0.4 mg/L calcium D-pantothenate, but larger in the presence of 0.002 mg/L calcium D-pantothenate, suggesting that, compared to strains Y5038 and Y2205, strain Y4720 had a higher growth rate on agar comprising the lower (R)-pantothenate concentration. Similar results were obtained using agar plates that completely lacked calcium D-pantothenate.

7.7 Example 7

This example demonstrates that omitting (R)-pantothenate increases the growth rate of yeast cells genetically engineered to produce higher levels of a heterologous HACD secondary metabolite and decreases the growth rate of yeast cells genetically engineered to produce lower levels of the heterologous secondary metabolite.

Four individual colonies of a number of yeast strains comprising heterologous enzymes including the MEV pathway enzymes: IPP isomerase, FPP synthase, and farnesene synthase, and capable of producing an exemplary HACD compound (farnesene) were inoculated in biomass build cultures consisting of wells of 96-well plates containing 360 μL of 2% sucrose BSM comprising either 10 mg/L or 0 mg/L calcium D-pantothenate. The biomass build cultures were grown for 72 hours at 34° C. in an ATR shaker at 1,000 rpm and 80% humidity, by which point the cultures had reached their maximal $OD_{600}$. The biomass build cultures were then diluted 1:25 into production cultures consisting of wells of a second set of 96-well plates containing 360 μL of 4% sucrose BSM comprising 10 mg/L calcium D-pantothenate. The production cultures were incubated for 48 hours in an ATR shaker at 1,000 rpm, 80% humidity, and 34° C., at which point samples were taken from each well to measure final biomass (final cell density) and farnesene titer as described in Examples 1 and 3 above, respectively.

As shown in FIG. 5, strains that produced farnesene at a yield of greater than 12% had greater biomass yield at lower (R)-pantothenate concentrations than at higher (R)-pantothenate concentrations. The opposite was true for strains that produced farnesene at a yield of less than 12%.

7.8 Example 8

This example demonstrates the phenomenon of strain degeneration which occurs when pantothenate is present in the culture medium, and thus HACD compound production is "on," during both the build and production stages of a fermentation process.

A 1 ml vial of frozen cell suspension of a yeast strain comprising heterologous enzymes including the MEV pathway enzymes: IPP isomerase, FPP synthase, and farnesene synthase, and capable of producing an exemplary HACD compound (farnesene), was thawed, transferred into a 250-ml baffled flask containing 50 ml of BSM 2.0 containing 2% sucrose and 10 mg/L calcium D-pantothenate, and grown in a shaker at 34° C., 200 RPM for 24 hours. The entire culture was then transferred into a 2.8 L Fernbach flask containing 850 ml of BSM 2.0 containing 2.0% sucrose and 10 mg/L calcium D-pantothenate, and grown in a shaker at 34° C., 250 RPM for 24 hours. The entire culture was then transferred into a 2 L fermentor. The nutrient feed to the fermentor was an undefined Brazilian cane syrup media comprising 10 mg/L calcium D-pantothenate, delivered with initial pulses equivalent to a 14 g/L/h sugar. The feed rate is then self-adjusted based on the fermentor demand for carbon, as indicated by rises in dissolved oxygen. The fermentation is run micro-aerobically at a constant temperature of 34° C., a constant pH of 4.5 (controlled by sodium hydroxide additions), and an initial oxygen transfer rate of 200 mmol $O_2$/L/h until the dissolved oxygen reached 0%, and then reduced to 100 mmol $O_2$/L/h for the remainder of the fermentation. Every three days, the volume of the tank is reduced to about 0.9 L to prevent overflow. Trace metals and vitamins missing in the cane syrup feed are replenished at that time. The amount of farnesene produced and the total consumed by the cells is monitored daily and the ratio of these two values (i.e., the product yield off of sugar) is determined for each 72 hour period and plotted as shown in FIG. 6. The product yield of the culture declines from its peak at 6 days to <65% of that peak by 21 days.

7.9 Example 9

This example demonstrates that omitting (R)-pantothenate during growth and storage of yeast cells genetically engineered to produce an exemplary HACD compound increases the production of the heterologous secondary metabolite by the yeast cells.

Yeast strain Y4954 comprises heterologous enzymes, including the following enzymes of the MEV pathway: IPP isomerase, FPP synthase, and farnesene synthase. This yeast strain is capable of producing farnesene at a yield of 13.6%.

Two sets of seed vials were prepared by inoculating half of a single colony of Y4954 cells into a 125 mL shake flask containing 15 mL of 2% sucrose BSM (seed vial medium) comprising 10 mg/L calcium D-pantothenate (seed vial medium, "+"), and the other half into a 125 mL shake flask containing 15 mL of 2% sucrose BSM (seed vial medium) comprising 0 mg/L calcium D-pantothenate (seed vial medium, "−"). Cells were grown at 30° C. in a shaker at 200 rpm until an $OD_{600}$ between 4 and 9 was reached, and until residual sucrose was around 3-6 g/L. Two parts sterile 50% glycerol solution was added to three parts cell broth, the suspension was aliquoted into seed vials, and the seed vials were slowly frozen to −80° C. at a rate of approximately −1° C./min.

Biomass build was accomplished by thawing one seed vial into a 250 mL shake flask containing 50 mL of 2% sucrose BSM (biomass build medium) comprising either 10 mg/L calcium D-pantothenate (biomass build medium, "+") or 0 mg/L calcium D-pantothenate (biomass build medium, "−"), and by growing the culture for 24 hours at 34° C. and 200 RPM. The culture was then transferred to a 1 L flask containing 800 mL of the same medium, and grown for an additional 48 hours.

For production of the exemplary HACD compound (farnesene), the seed build culture was transferred to a 2 L bench top fermentor containing production medium comprising 10 mg/L calcium D-pantothenate (production medium, "+"), and the culture was incubated for 6 days following a feeding protocol that maximized farnesene yield.

As shown in Table 1, Y4954 cells produced a higher farnesene yield when (R)-pantothenate was omitted from the seed vial medium. They produced an even higher farnesene yield when (R)-pantothenate was also omitted from the biomass build medium.

Table 1 also shows that omitting (R)-pantothenate in the seed vial and biomass build media does not irreversibly compromise the ability of the host cells to produce farnesene when provided with (R)-pantothenate during the production phase. In fact, the use of a seed medium and biomass build media having reduced or absent in (R)-pantothenate, followed by production phase culture in a production medium containing (R)-pantothenate results in the best production of the heterologous HACD compounds.

TABLE 1

Heterologous Farnesene Production by Y4954 Cells Stored and Grown in Absence or Presence of Calcium D-pantothenate

| Seed Vial Medium | Biomass Build Medium | Production Medium | Final Relative Farnesene Yield |
|---|---|---|---|
| + | + | + | 57% |
| − | + | + | 72% |
| − | − | + | 100% |

"+" = 10 mg/L calcium D-pantothenate in medium.
"−" = 0 mg/L calcium D-pantothenate in medium.

All publications, patents and patent applications cited in this specification are herein incorporated by reference as if each individual publication or patent application were specifically and individually indicated to be incorporated by reference. Various modifications and variations of the present disclosure will be apparent to those skilled in the art without departing from the scope and spirit of the disclosure. Although the disclosure has been described in some detail by way of illustration and example for purposes of clarity of understanding, it will be readily apparent to those of ordinary skill in the art in light of the teachings provided herein that certain changes and modifications may be made thereto without departing from the spirit or scope of the appended claims, and that the claims should not be unduly limited to such specific embodiments. Indeed, various modifications of the described modes for carrying out the disclosure, which are understood by those skilled in the art, are intended to be within the scope of the claims.

What is claimed is:

1. A method of producing an isoprenoid comprising:
   (a) providing a host cell that is genetically modified to comprise an exogenous nucleic acid encoding one or more enzymes of the mevalonate (MEV) pathway chromosomally integrated into the host genome to produce an isoprenoid from the MEV pathway in a greater amount compared to a parent host cell lacking said genetic modification, wherein the one or more enzymes of the MEV pathway are selected from the group consisting of:
      (i) an enzyme that condenses two molecules of acetyl-coenzyme A to form acetoacetyl-CoA;
      (ii) an enzyme that condenses acetoacetyl-CoA with another molecule of acetyl-CoA to form 3-hydroxy-3-methylglutaryl-CoA (HMG-CoA);
      (iii) an enzyme that converts HMG-CoA into mevalonate;
      (iv) an enzyme that converts mevalonate into mevalonate 5-phosphate;
      (v) an enzyme that converts mevalonate 5-phosphate into mevalonate 5-pyrophosphate;
      (vi) an enzyme that converts mevalonate 5-pyrophosphate into IPP;
      (vii) an enzyme that converts IPP into DMAPP;
      (viii) a polyprenyl synthase that can condense IPP and/or DMAPP molecules to form polyprenyl compounds containing more than five carbons;
      (ix) an enzyme that condenses IPP with DMAPP to form GPP;
      (x) an enzyme that condenses two molecules of IPP with one molecule of DMAPP;
      (xi) an enzyme that condenses IPP with GPP to form FPP;
      (xii) an enzyme that condenses IPP and DMAPP to form GGPP; and
      (xiii) an enzyme that condenses IPP and FPP to form GGPP;
   (b) culturing a single strain of the host cell that is genetically modified in a build stage to produce an inoculum, wherein a population of the host cell that is genetically modified is cultured for a period of time sufficient for said population to undergo a plurality of doublings in an aqueous culture medium comprising a carbon source and a limiting amount of exogenously-provided pantothenate below 0.2 mg/L, wherein the limiting amount of pantothenate limits the production of isoprenoid from the MEV pathway by the population; followed by
   (c) culturing the population or subpopulation thereof of the host cell that is genetically modified in a production stage for a period of 3 to 20 days, wherein said inoculum is transferred to an aqueous culture medium comprising a carbon source and a non-limiting amount of exogenously-provided pantothenate above 0.2 mg/L, wherein isoprenoid production from the MEV pathway by the population or subpopulation thereof is increased in the presence of the non-limiting amount of pantothenate.

2. The method of claim 1, wherein the limiting amount of exogenously-provided pantothenate is 0 mg/L.

3. The method of claim 1, wherein the non-limiting amount of exogenously-provided pantothenate is 10 mg/L.

4. The method of claim 1, wherein the increased isoprenoid production by the host cell that is genetically modified is expressed in terms of improved yield (gram of isoprenoid produced per gram of carbon substrate) or improved productivity (grams of isoprenoid produced per liter of culture medium per hour).

5. The method of claim 1, further comprising recovering the isoprenoid.

6. The method of claim 1, wherein the pantothenate is (R)-pantothenate or any salt thereof.

7. The method of claim 1, wherein the host cell that is genetically modified is selected from the group consisting of a fungal cell, a bacterial cell, a plant cell, and an animal cell.

8. The method of claim 1, wherein the host cell that is genetically modified is a yeast cell.

9. The method of claim 1, wherein the host cell that is genetically modified further comprises an exogenous nucleic acid encoding an enzyme that modifies a polyprenyl, selected from the group consisting of a geraniol synthase, a linalool synthase, a limonene synthase, a myrcene synthase, an ocimene synthase, an α-pinene synthase, β-pinene synthase, a sabinene synthase, a γ-terpinene synthase, a terpinolene synthase, an amorphadiene synthase, an α-farnesene synthase, a β-farnesene synthase, a farnesol synthase, a nerolidol synthase, a patchoulol synthase, a nootkatone synthase, and abietadiene synthase.

10. The method of claim 1, wherein the limiting amount of exogenously-provided pantothenate is below 0.1 mg/L.

11. The method of claim 1, wherein in step (b), the build stage is carried out until the population of the host cell that is genetically modified reaches an $OD_{600}$ of at least 10.

12. A method of producing an isoprenoid comprising:
   (a) prior to a build stage, providing a host cell that is genetically modified to comprise an exogenous nucleic acid encoding one or more enzymes of the mevalonate (MEV) pathway chromosomally integrated into the host genome to produce an isoprenoid from the MEV pathway in a greater amount compared to a parent host cell lacking said genetic modification, wherein the one or more enzymes of the MEV pathway are selected from the group consisting of:
      (i) an enzyme that condenses two molecules of acetyl-coenzyme A to form acetoacetyl-CoA;
      (ii) an enzyme that condenses acetoacetyl-CoA with another molecule of acetyl-CoA to form 3-hydroxy-3-methylglutaryl-CoA (HMG-CoA);
      (iii) an enzyme that converts HMG-CoA into mevalonate;
      (iv) an enzyme that converts mevalonate into mevalonate 5-phosphate;
      (v) an enzyme that converts mevalonate 5-phosphate into mevalonate 5-pyrophosphate;
      (vi) an enzyme that converts mevalonate 5-pyrophosphate into IPP;
      (vii) an enzyme that converts IPP into DMAPP;

(viii) a polyprenyl synthase that can condense IPP and/or DMAPP molecules to form polyprenyl compounds containing more than five carbons;

(ix) an enzyme that condenses IPP with DMAPP to form GPP;

(x) an enzyme that condenses two molecules of IPP with one molecule of DMAPP;

(xi) an enzyme that condenses IPP with GPP to form FPP;

(xii) an enzyme that condenses IPP and DMAPP to form GGPP; and, (xiii) an enzyme that condenses IPP and FPP to form GGPP;

(b) producing an inoculum of the host cell that is genetically modified in an aqueous culture medium comprising a carbon source and lacking exogenously-provided pantothenate during the build stage; followed by (c) culturing said inoculum from step (b) in a culture medium comprising a carbon source and supplemented with at least 1 mg/L of exogenously-provided pantothenate during a production stage.

13. The method of claim 12, wherein producing said inoculum comprises culturing a population of said host cell that is genetically modified for a period of time sufficient for said population to undergo a plurality of doublings.

14. The method of claim 12, wherein said culturing of step (c) is carried out for a period of 3 to 20 days.

* * * * *